United States Patent
DiCosimo et al.

(10) Patent No.: US 7,951,567 B2
(45) Date of Patent: *May 31, 2011

(54) PRODUCTION OF PERACIDS USING AN ENZYME HAVING PERHYDROLYSIS ACTIVITY

(75) Inventors: Robert DiCosimo, Chadds Ford, PA (US); John Edward Gavagan, Wilmington, DE (US); Mark Scott Payne, Wilmington, DE (US); Frederick B. Cooling, III, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/691,856

(22) Filed: Jan. 22, 2010

(65) Prior Publication Data

US 2010/0152292 A1    Jun. 17, 2010

Related U.S. Application Data

(62) Division of application No. 11/638,635, filed on Dec. 12, 2006.

(60) Provisional application No. 60/750,092, filed on Dec. 13, 2005, provisional application No. 60/853,065, filed on Oct. 20, 2006.

(51) Int. Cl.
*C12P 7/40* (2006.01)
*C12N 9/14* (2006.01)
*C12N 9/18* (2006.01)
*C12N 15/00* (2006.01)
*C12N 1/21* (2006.01)

(52) U.S. Cl. ............ 435/136; 435/197; 435/321.1; 435/252.3

(58) Field of Classification Search .............. None
See application file for complete search history.

(56) References Cited

U.S. PATENT DOCUMENTS

| | | |
|---|---|---|
| 3,974,082 A | 8/1976 | Weyn et al. |
| 4,444,886 A | 4/1984 | Esders et al. |
| 4,585,150 A | 4/1986 | Beacham et al. |
| 5,108,457 A * | 4/1992 | Poulose et al. .............. 8/111 |
| 5,116,575 A | 5/1992 | Badertscher et al. |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,624,634 A | 4/1997 | Brougham et al. |
| 5,683,724 A | 11/1997 | Hei et al. |
| 5,932,532 A | 8/1999 | Ghosh et al. |
| 6,183,807 B1 | 2/2001 | Gutzmann et al. |
| 6,210,639 B1 | 4/2001 | Vlass et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,645,233 B1 | 11/2003 | Ayers et al. |
| 7,384,787 B2 * | 6/2008 | Kazlauskas et al. .......... 435/440 |
| 2003/0026846 A1 | 2/2003 | Hei et al. |
| 2005/0008526 A1 | 1/2005 | Bianchetti et al. |
| 2005/0139608 A1 | 6/2005 | Muehlhausen et al. |

FOREIGN PATENT DOCUMENTS

| | | |
|---|---|---|
| EP | 0807156 B1 | 3/2001 |
| WO | WO9903984 A2 | 1/1999 |
| WO | WO00/11713 A1 | 3/2000 |
| WO | WO2004/058961 A1 | 7/2004 |
| WO | WO2007/070609 A2 | 6/2007 |
| WO | WO2008/073139 A1 | 6/2008 |

OTHER PUBLICATIONS

Chica et al. Curr Opin Biotechnol. Aug. 2005; 16(4):378-84.*
Witkowski et al. Biochemistry. Sep. 7, 1999; 38(36): 11643-50.*
Seffernick et al. J Bacteriol. Apr. 2001; 183 (8): 2405-10.*
U.S. Appl. No. 11/413,246, filed Apr. 28, 2006, Robert DiCosimo et al.
U.S. Appl. No. 11/588,523, filed Oct. 27, 2006, Robert DiCosimo et al.
Daniel Swern, Organic Peroxides, vol. 1, pp. 313-516; Wiley Interscience, 1971 (Book Not Included).
O. Kirk et al. Enzyme Catalyzed Degradation and Formation of Peroxycarboxylic Acids, Biocatalysis, vol. 11, pp. 65-77, 1994.
Lennon et al., The I.M.A.G.E. Consortium: An Intergrated Molecular Analysis of Genomes and Their Expression, Genomics, vol. 33, pp. 151-152, 1996.
Mitsushima et al., Gene Cloning, Nucleotide Sequence, and Expression of a Cephalosporin-C Deacetylase From Bacillus . . . , Appl. Env. Microbiol., vol. 61(6), pp. 2224-2229, 1995.
Vincent et al., Multifunctional Xylooligosaccharide/Cephalosporin C Deacetylase Revealed by the . . . at 1.9A Resolution, J. Mol. Biol., vol. 330, pp. 593-606, 2003.
Gordon F. Bickerstaff, Immobilization of Enzymes and Cells, 1997. (Book Not Included).
Mitsushima et al, National Center for Biotechnology Info Gen. Id. No. 550075, Gene Cloning, Nucleotide Sequence & Expression Accession No. BAA01729.1, pp. 1-2, 1999.
Payne et al., Use of Alkaline Phosphatase Fusions to Studt Protein Secretion in *Bacillus subtilis*, J. Bacteriol., vol. 173, pp. 2278-2282, 1991.
Sambrook et al., Molecular Cloning: A Laboratory Manual, Third Edition, Cold Spring Harbor Laboratory Press, 2001. (Book Not Included).
A. M. Lesk, Computational Molecular Biology, Oxford University Press, 1988. (Book Not Included).

(Continued)

*Primary Examiner* — Robert Mondesi
*Assistant Examiner* — Younus Meah

(57) ABSTRACT

A method is provided for producing peroxycarboxylic acids from carboxylic acid esters. More specifically, carboxylic acid esters are reacted with an inorganic peroxide, such as hydrogen peroxide, in the presence of an enzyme catalyst having perhydrolysis activity derived from *Bacillus* sp. to produce peroxycarboxylic acids.

25 Claims, No Drawings

OTHER PUBLICATIONS

D. W. Smith, Biocomputing: Informatics and Genome Projects, Academic Press, 1993. (Book Not Included).
Griffin et al., Computer Analysis of Sequence Data, Part I, Human Press, 1994. (Book Not Included).
G. Von Heinje, Sequence Analysis in Molecular Biology, Academic Press, 1987. (Book Not Included).
M. Gribskov et al., Sequence Analysis Primer, Stockton Press, 1991, (Book Not Included).
Higgins et al., Fast and Sensitive Multiple Sequence Alignments on a Microcomputer, CABIOS, vol. 5, pp. 151-153, 1989.
Altschul et al., Basic Local Alignment Search Tool, J. Mol. Biol. vol. 215, pp. 403-410, 1990.
Pearson, Searching Protein Sequence Databases is Optimal Best? Comput. Methods Genome Res., [Proc. Int. Symp.] (1994), Meeting Date 1992, pp. 111-120.
Bickerstaff, Immobilization of Enzymes and Cells; Human Press, 1997 (Book Not Included).
Karst et al., Simultaneous HPLC Determination of Peroxyacetic Acid and Hydrogen Peroxide, Anal. Chem., vol. 69 (17) pp. 3623-3627,1997.
Minning, et al., Determination of Peracid and Putative Enzymatic Peracid Formation by an Easy Colorimetric Assay, Analytica Chimica Acta, vol. 378, pp. 293-298, 1999.
J. Gabrielson et al., Evaluation of Redox Indicators and the Use of Digital Scanners and . . . Growth in Microplates., J. Microbiol. Methods, vol. 50, pp. 63-73, 2002.
Brock, Disinfection, Sterilization, and Preservation, 5th edition, Lippincott Williams & Wilkins, 2001. (Book Not Included).
Abbott et al., Physical Properties and Kinetic Behavior of a Cephalosporin Acetylesterase Produced by *Bacillus subtilis*, Appl. Microbiol., vol. 30(3), pp. 413-419, 1975.
Politino et al., Purification and Characterization of a Cephalosporin Esterase from Rhodosporidium Toruloides, Appl. Environ. Microbiol., vol. 63, 4807-4811,1997.
Sakai et al., Purification and Properties of Cephalosporin-C Deacetylase from the Yeast . . . , J. Ferment Bioeng. vol. 85, pp. 53-57. 1998.
Lorenz et. al., Isolation, Analysis and Expression of two Genes from *Thermoanaerobacterium* Sp. Strain . . . , Bacterial, vol. 179, pp. 5436-5441, 1997.
Cardoza et al. A Cephalosporin C Acetylhydrolase is Present in the Cultures of Nocardia Lactamdurans, Appl. Microbiol. Biotechnol.,vol. 54(3), pp. 406-412, 2000.
Takami et al., Complete Genome Sequence of the . . . Bacterium *Bacillus halodurans* & Genomic Sequence Comparison with *Bacillus subtilis*, NAR, vol. 28(21), pp. 4317-4331, 2000.
Rey et al., Complete Genome Sequence of the Industrial Bacterium *Bacillus licheniformis* and Comparisons with Closley . . . , Genome Biol., vol. 5(10), Article 77,pp. 1-13, 2004.
Degrassi et al., The Acetyl Xylan Esterase of *Bacillus pumilus* Belongs to a Family of Esterases with Broad Substrate Specificity, Microbiology., vol. 146, pp. 1585-1591, 2000.
Brock, Biotechnology: A Textbook of Industrial Microbiology, Second Edition, 1989. (Book Not Included).
Deshpande et al., Ethanol Production from Cellulose by Coupled Saccharification/Fermentation Using . . . , Appl. Biochem. Biotechnol., vol. 36, pp. 227-234, 1992.
Sulter et al., Proliferation and Metabolic Significance of Peroxisomes in Canadian . . . , Arch. Microbiol., vol. 153, pp. 485-489, 1990.
Copeland A. et al., "Thermotoga Lettingae Acetyl Xylan Esterase", A8F440_THELT, XP002501372, Nov. 13, 2007.
Bernhardt, P., et al., "Molecular Basis of Perhydrolase Activity in Serine Hydrolases", Angewandte Chemie, vol. 44, pp. 2742-2746 (2005).
Bernhard, P., et al., Supporting Information for "Molecular Basis of Perhydrolase Activity in Serine Hydrolases", vol. 44, pp. 2742-2746 (2005).

* cited by examiner

SEQUENCE LISTING

<160> NUMBER OF SEQ ID NOS: 26

<210> SEQ ID NO 1
<211> LENGTH: 960
<212> TYPE: DNA
<213> ORGANISM: Bacillus subtilis

```
<220> FEATURE:
<221> NAME/KEY: CDS
<222> LOCATION: (1)..(960)
<220> FEATURE:
<221> NAME/KEY: misc_feature
<222> LOCATION: (1)..(960)
<223> OTHER INFORMATION: Bacillus subtilis ATCC 31954

<400> SEQUENCE: 1 atg caa cta ttc gat ctg ccg ctc gac caa ttg caa aca tat aag cct        48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg        96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac       144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc       192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc       240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat       288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca       336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att       384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat       432
Ser Leu His Gly His Ala Leu Gly Trp Met Thr Lys Gly Ile Leu Asp
    130                 135                 140 aaa gat aca tac tat tac cgc ggt gtt tat ttg gac gcc gtc cgc gcg       480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt       528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg       576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc       624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa       672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag       720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga       768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg       816
Val Lys Val Pro Val Leu Met Ser Ile Gly Leu Ile Asp Lys Val Thr
            260                 265                 270 ccg ccg tcc acc gtg ttt gcc gcc tac aat cat ttg gaa aca gag aaa       864
Pro Pro Ser Thr Val Phe Ala Ala Tyr Asn His Leu Glu Thr Glu Lys
```

```
                   275                 280                 285
gag ctg aag gtg tac cgc tac ttc gga cat gag tat atc cct gct ttt      912
Glu Leu Lys Val Tyr Arg Tyr Phe Gly His Glu Tyr Ile Pro Ala Phe
290                 295                 300 caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315
```

<210> SEQ ID NO 2
<211> LENGTH: 318
<212> TYPE: PRT
<213> ORGANISM: Bacillus subtilis

<400> SEQUENCE: 2

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
        50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315
```

<210> SEQ ID NO 3

-continued

```
<211> LENGTH: 24
<212> TYPE: DNA
<213> ORGANISM: artificial sequence
<220> FEATURE:
<223> OTHER INFORMATION: Primer

<400> SEQUENCE: 3
atgcaactat tcgatctgcc gctc                                              24

<210> SEQ ID NO 4
<211> LENGTH: 26
<212> TYPE: DNA
<213> ORGANISM: artificial sequence
<220> FEATURE:
<223> OTHER INFORMATION: Primer

<400> SEQUENCE: 4
ttatcagcct ttaagatgct gcttaa                                            26

<210> SEQ ID NO 5
<211> LENGTH: 957
<212> TYPE: DNA
<213> ORGANISM: Bacillus subtilis
<220> FEATURE:
<221> NAME/KEY: misc_feature
<222> LOCATION: (1)..(957)
<223> OTHER INFORMATION: Bacillus subtilis subsp. subtilis strain 168

<400> SEQUENCE: 5
atgcaactat tcgatctgcc gctcgaccaa ttgcaaacat ataagcctga aaaaacagca        60
ccgaaagatt tttctgagtt ttggaaattg tctttggagg aacttgcaaa agtccaagca       120
gaacctgatt tacagccggt tgactatcct gctgacggag taaaagtgta ccgtctcaca       180
tataaaagct tcggaaacgc ccgcattacc ggatggtacg cggtgcctga caaggaaggc       240
ccgcatccgg cgatcgtgaa atatcatggc tacaatgcaa gctatgatgg tgagattcat       300
gaaatggtaa actgggcact ccatggctac gccacattcg gcatgcttgt ccgcggccag       360
cagagcagcg aggatacgag tatttcaccg cacggtcacg cttttgggctg gatgacgaaa      420 ggaattcttg ataaagatac atactattac cgcggtgttt atttggacgc cgtccgcgcg       480
cttgaggtca tcagcagctt cgacgaggtt gacgaaacaa ggatcggtgt gacaggagga       540
agccaaggcg aggtttaac cattgccgca gcagcgctgt cagacattcc aaaagccgcg       600
gttgccgatt atccttattt aagcaacttc gaacgggcca ttgatgtggc gcttgaacag       660
ccgtaccttg aaatcaattc cttcttcaga gaaatggca gcccggaaac agaagtgcag       720
gcgatgaaga cactttcata tttcgatatt atgaatctcg ctgaccgagt gaaggtgcct       780
gtcctgatgt caatcggcct gattgacaag gtcacgccgc cgtccaccgt gtttgccgcc       840
tacaatcatt tggaaacaaa gaaagagctg aaggtgtacc gctacttcgg acatgagtat       900
atccctgctt tcaaaactga aaacttgct ttctttaagc agcatcttaa aggctga          957

<210> SEQ ID NO 6
<211> LENGTH: 318
<212> TYPE: PRT
<213> ORGANISM: Bacillus subtilis
<220> FEATURE:
<221> NAME/KEY: MISC_FEATURE
<222> LOCATION: (1)..(318)
<223> OTHER INFORMATION: Bacillus subtilis subsp. subtilis strain 168

<400> SEQUENCE: 6

Met Gln Leu Phe Asp Leu Pro Leu Asp Gln Leu Gln Thr Tyr Lys Pro
1               5                   10                  15
```

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
            115                 120                 125

Ser Pro His Gly His Ala Leu Gly Trp Met Thr Lys Gly Ile Leu Asp
        130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 7
<211> LENGTH: 957
<212> TYPE: DNA
<213> ORGANISM: Bacillus subtilis
<220> FEATURE:
<221> NAME/KEY: misc_feature
<222> LOCATION: (1)..(957)
<223> OTHER INFORMATION: Bacillus subtilis ATCC 6633

<400> SEQUENCE: 7
atgcaactat tcgatctgcc gctcgaccaa ttgcaaacgt ataagcctga aaaacaaca      60 ccgaacgatt tttctgagtt ttggaaatcg tctttggacg aacttgcgaa agtcaaagca     120
gcacctgatt tacagctggt tgattatcct gctgatggag tcaaggtgta ccgcctcaca     180
tataaaagct tcggaaacgc ccgcattacc ggatggtacg cagtgcctga caaggaagga     240
ccgcatccgg cgatcgtcaa atatcatggc tacaacgcta gctatgacgg tgagattcat     300

```
gaaatggtaa actgggcgct ccacggttac gccgcattcg gcatgctagt ccgcggccag        360
cagagcagcg aggatacgag tatttctcca catggccatg ctttgggctg atgacgaaa         420 ggaatccttg ataaagatac atactattac cggggcgttt atttggacgc tgtccgcgcg        480
cttgaggtca tcagcagctt tgacgaagtt gacgaaacaa gaatcggtgt gacaggcgga        540
agccaaggag gcggcttaac cattgccgca gccgctctgt cagacattcc aaaagccgcg        600
gttgccgatt atccttattt aagcaacttt gaacgggcca ttgatgtggc gcttgaacag        660
ccgtaccttg aaatcaattc cttctttaga gaaatggaa gcccggaaac ggaagagaag         720
gcgatgaaga cactttcata tttcgatatt atgaatctcg ctgaccgagt gaaggtccct        780
gtcctgatgt cgatcggtct gattgacaag gtcacgccgc cgtccaccgt gtttgccgca        840
tacaaccact tggagacaga gaaagagctc aaagtgtacc gctacttcgg gcatgagtat        900
atccctgcct ttcaaacaga aaaacttgct ttctttaagc agcatcttaa aggctga          957

<210> SEQ ID NO 8
<211> LENGTH: 318
<212> TYPE: PRT
<213> ORGANISM: Bacillus subtilis
<220> FEATURE:
<221> NAME/KEY: MISC_FEATURE
<222> LOCATION: (1)..(318)
<223> OTHER INFORMATION: Bacillus subtilis ATCC 6633

<400> SEQUENCE: 8

Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
```

```
            245                 250                 255
Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
            290                 295                 300

Gln Thr Glu Lys Leu Ala Phe Phe Lys Gln His Leu Lys Gly
305                 310                 315
```

<210> SEQ ID NO 9
<211> LENGTH: 957
<212> TYPE: DNA
<213> ORGANISM: Bacillus licheniformis
<220> FEATURE:
<221> NAME/KEY: misc_feature
<222> LOCATION: (1)..(957)
<223> OTHER INFORMATION: Bacillus licheniformis ATCC 14580

<400> SEQUENCE: 9

```
atgcagcagc cttatgatat gccgcttgaa cagctttatc agtataaacc tgaacggacg    60
gcaccggccg attttaaaga gttctggaag ggttcattgg aggaattggc aaatgaaaaa   120
gcggaccgc  agcttgaacc gcatgaatat ccggctgacg gggtaaaagt ctactggctt   180
acatacagaa gcatcggggg agcgcgaatt aaaggctggt acgcagtacc cgaccgccaa   240
gggcctcatc ctgcgatcgt caaataccac ggctataacg caagctatga cggagacatt   300
cacgatattg tcaattgggc tcttcacggc tatgcggcat tcggtatgct ggtccgcgga   360
cagaacagca gtgaagatac agagatctct catcacggac atgtacccgg ctggatgaca   420
aaaggaatcc tcgatccgaa aacatattac tacagagggg tctatttaga tgccgtacga   480
gcagtcgaag tggtcagcgg ttttgctgaa gtcgatgaaa agcggatcgg ggtgatcggg   540
gcaagccaag gaggcgggct ggccgtcgcg gtttcggcgc tgtccgatat tccaaaagca   600
gccgtgtcag ataccctta tttaagcaat tttcaacgag cgatcgatac agcgatcgac   660
cagccatatc tcgaaatcaa ctccttttc agaagaaaca ccagtccgga tattgagcag   720
gcggccatgc ataccctgtc ttatttcgat gtcatgaacc ttgcccaatt ggtcaaagcg   780
accgtactca tgtcgatcgg actggttgac accatcactc cgccatccac cgtctttgcg   840
gcttacaatc acttggaaac ggataaagaa ataaaagtgt accgttattt tggacacgaa   900
tacatcccgc cgttccaaac cgaaaagctg gcgtttctga aaagcatct gaaataa       957
```

<210> SEQ ID NO 10
<211> LENGTH: 318
<212> TYPE: PRT
<213> ORGANISM: Bacillus licheniformis
<220> FEATURE:
<221> NAME/KEY: MISC_FEATURE
<222> LOCATION: (1)..(318)
<223> OTHER INFORMATION: Bacillus licheniformis ATCC 14580

<400> SEQUENCE: 10

```
Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
```

```
                50              55              60
Ile Gly Gly Ala Arg Ile Lys Gly Trp Tyr Ala Val Pro Asp Arg Gln
 65              70              75              80

Gly Pro His Pro Ala Ile Val Lys Tyr His Gly Tyr Asn Ala Ser Tyr
                85              90              95

Asp Gly Asp Ile His Asp Ile Val Asn Trp Ala Leu His Gly Tyr Ala
               100             105             110

Ala Phe Gly Met Leu Val Arg Gly Gln Asn Ser Ser Glu Asp Thr Glu
               115             120             125

Ile Ser His His Gly His Val Pro Gly Trp Met Thr Lys Gly Ile Leu
130             135             140

Asp Pro Lys Thr Tyr Tyr Tyr Arg Gly Val Tyr Leu Asp Ala Val Arg
145             150             155             160

Ala Val Glu Val Val Ser Gly Phe Ala Glu Val Asp Glu Lys Arg Ile
               165             170             175

Gly Val Ile Gly Ala Ser Gln Gly Gly Gly Leu Ala Val Ala Val Ser
               180             185             190

Ala Leu Ser Asp Ile Pro Lys Ala Ala Val Ser Glu Tyr Pro Tyr Leu
               195             200             205

Ser Asn Phe Gln Arg Ala Ile Asp Thr Ala Ile Asp Gln Pro Tyr Leu
210             215             220

Glu Ile Asn Ser Phe Phe Arg Arg Asn Thr Ser Pro Asp Ile Glu Gln
225             230             235             240

Ala Ala Met His Thr Leu Ser Tyr Phe Asp Val Met Asn Leu Ala Gln
               245             250             255

Leu Val Lys Ala Thr Val Leu Met Ser Ile Gly Leu Val Asp Thr Ile
               260             265             270

Thr Pro Pro Ser Thr Val Phe Ala Ala Tyr Asn His Leu Glu Thr Asp
               275             280             285

Lys Glu Ile Lys Val Tyr Arg Tyr Phe Gly His Glu Tyr Ile Pro Pro
               290             295             300

Phe Gln Thr Glu Lys Leu Ala Phe Leu Arg Lys His Leu Lys
305             310             315

<210> SEQ ID NO 11
<211> LENGTH: 963
<212> TYPE: DNA
<213> ORGANISM: Bacillus pumilis

<400> SEQUENCE: 11
atgcaattgt tcgatttatc actagaagag ctaaaaaaat ataaaccaaa gaaaacagca      60
cgtcctgatt tctcagactt ttggaagaaa tcgctcgaag aactgcgcca agtggaggca     120
gagccaacac ttgaatctta tgactatcca gtgaaaggcg tcaaggtgta ccgcctgacg     180
tatcaaagct tggacattca taaaattgaa ggcttttatg ctgtgcctga tcaaactggt     240
ccgcatccag cgctcgttcg ttttcatggc tataatgcca gctatgacgg cggcattcac     300
gacatcgtca actgggcgct gcacggctat gcaacatttg gtatgctcgt ccgcggtcaa     360
ggtggcagtg aagacacatc agtgacacca ggcgggcatg cattagggtg gatgacaaaa     420
ggcattttat cgaaagatac gtactattat cgaggcgttt atctagatgc tgttcgtgca     480
cttgaagtca ttcagtcttt ccccgaagta gatgaacacc gtatcggcgt gatcggtgga     540
agtcaggggg gtgcgttagc gattgcggcg cagccctttt cagacattcc aaaagtcgtt     600
gtggcagact atccttactt atcaaatttt gagcgtgcag ttgatgttgc cttggagcag     660
```

-continued

```
ccttatttag aaatcaattc atactttcgc agaaacagtg atccgaaagt ggaggaaaag    720
gcatttgaga cattaagcta ttttgattta atcaatttag ctggatgggt gaaacagcca    780
acattgatgg cgatcggtct gattgacaaa ataaccccac catctactgt gtttgcggca    840
tacaaccatt tagaaacaga taaagacctg aaagtatatc gctattttgg acacgagttt    900
atccctgctt ttcaaacaga gaagctgtcc tttttacaaa agcatttgct tctatcaaca    960
taa                                                                  963
```

<210> SEQ ID NO 12
<211> LENGTH: 320
<212> TYPE: PRT
<213> ORGANISM: Bacillus pumilis

<400> SEQUENCE: 12

```
Met Gln Leu Phe Asp Leu Ser Leu Glu Glu Leu Lys Lys Tyr Lys Pro
 1               5                  10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
           100                 105                 110

Phe Gly Met Leu Val Arg Gly Gln Gly Gly Ser Glu Asp Thr Ser Val
       115                 120                 125

Thr Pro Gly Gly His Ala Leu Gly Trp Met Thr Lys Gly Ile Leu Ser
   130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala
            180                 185                 190

Leu Ser Asp Ile Pro Lys Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320
```

<210> SEQ ID NO 13
<211> LENGTH: 963
<212> TYPE: DNA
<213> ORGANISM: Clostridium thermocellum
<220> FEATURE:
<221> NAME/KEY: misc_feature
<222> LOCATION: (1)..(963)
<223> OTHER INFORMATION: Clostridium thermocellum ATCC 27405

<400> SEQUENCE: 13

```
atggcacaat tatatgatat gcctttggag gaattaaaaa aatataagcc tgcgcttaca    60
aaacagaaag attttgatga gttttgggaa aaaagcctta agagctggc tgaaattcct   120
ttaaaatatc aacttatacc ttatgatttt ccggcccgga gggtaaaagt tttcagagtt   180
gaatatcttg gttttaaagg tgcaaatatt gaagggtggc ttgccgttcc cgagggagaa   240
gggttgtatc ccgggcttgt acagtttcac ggatacaact gggcgatgga tggatgtgtt   300
cccgatgtgg taaattgggc tttgaatgga tatgccgcat ttcttatgct tgttcgggga   360
cagcagggaa gaagcgtgga caatattgtg cccggcagcg gtcatgcttt gggatggatg   420
tcgaaaggta ttttgtcacc ggaggaatat tattatagag gagtatatat ggatgcggtt   480
cgtgctgttg aaattttggc ttcgcttcct tgtgtggatg aatcgagaat aggagtgaca   540
gggggcagcc agggtggagg acttgcactg gcggtggctg ctctgtccgg cataccgaaa   600
gttgcagccg tgcattatcc gttctggca cattttgagc gtgccattga cgttgcgccg   660
gacggccctt atcttgaaat taacgaatat ttaagaagaa acagcggtga agaaatagaa   720
agacaggtaa agaaaaccct ttcctatttt gatatcatga atcttgctcc ccgtataaaa   780
tgccgtactt ggatttgcac tggtcttgtg gatgagatta ctcctccgtc aacggttttt   840
gcagtgtaca atcacctcaa atgcccaaag gaaatttcgg tattcagata ttttgggcat   900
gaacatatgc caggaagcgt tgaaatcaag ctgaggatac ttatggatga gctgaatccg   960
taa                                                                963
```

<210> SEQ ID NO 14
<211> LENGTH: 320
<212> TYPE: PRT
<213> ORGANISM: Clostridium thermocellum
<220> FEATURE:
<221> NAME/KEY: MISC_FEATURE
<222> LOCATION: (1)..(320)
<223> OTHER INFORMATION: Clostridium thermocellum ATCC 27405

<400> SEQUENCE: 14

```
Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
```

```
                115                 120                 125
Ile Val Pro Gly Ser Gly His Ala Leu Gly Trp Met Ser Lys Gly Ile
            130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Leu Ala Leu Ala Val
            180                 185                 190

Ala Ala Leu Ser Gly Ile Pro Lys Val Ala Ala Val His Tyr Pro Phe
                195                 200                 205

Leu Ala His Phe Glu Arg Ala Ile Asp Val Ala Pro Asp Gly Pro Tyr
            210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
            275                 280                 285

Pro Lys Glu Ile Ser Val Phe Arg Tyr Phe Gly His Glu His Met Pro
            290                 295                 300

Gly Ser Val Glu Ile Lys Leu Arg Ile Leu Met Asp Glu Leu Asn Pro
305                 310                 315                 320

<210> SEQ ID NO 15
<211> LENGTH: 978
<212> TYPE: DNA
<213> ORGANISM: Thermotoga neapolitana

<400> SEQUENCE: 15
atggccttct tcgatatgcc ccttgaggaa ctgaaaaagt accggcctga aaggtacgag      60
gagaaagatt tcgatgagtt ctggagggaa acacttaaag aaagcgaagg attccctctg     120
gatcccgtct ttgaaaaggt ggactttcat ctcaaaacgg ttgaaacgta cgatgttact     180
ttctctggat acaggggca gagaataaag ggctggcttc ttgttccgaa gttggcggaa      240
gaaaagcttc catgcgtcgt gcagtacata ggttacaatg gtggaagggg ttttccacac     300
gactggctgt tctggccgtc aatgggttac atctgttttg tcatggacac caggggggcag    360
ggaagcggct ggatgaaggg agacacaccg gattaccctg agggtccagt cgatccacag     420
taccccggat tcatgacgag gggcattctg gatccgggaa cctattacta caggcgagtc     480
ttcgtggatg cggtcagggc ggtggaagca gccatttcct tcccgagagt ggattccagg     540
aaggtggtgg tggccggagg cagtcagggt ggggggaatcg cccttgcggt gagtgccctg    600
tcgaacaggg tgaaggctct gctctgcgat gtgccgtttc tgtgccactt cagaagggcc     660
gtgcaacttg tcgacacaca cccatacgtg gagatcacca acttcctcaa aacccacagg     720
gacaaagagg agattgtttt cagaacactt tcctacttcg atggtgtgaa ctttgcagca     780
agggcaaagg tgcccgccct gttttccgtt gggctcatgg acaccatctg tcctccctcg     840
acggtcttcg ccgcttacaa ccactacgcc ggtccaaagg agatcagaat ctatccgtac     900
aacaaccacg aaggtggagg ttctttccag gcaattgagc aggtgaaatt cttgaagaga     960
ctatttgagg aaggctag                                                   978
```

<210> SEQ ID NO 16
<211> LENGTH: 325
<212> TYPE: PRT
<213> ORGANISM: Thermotoga neapolitana

<400> SEQUENCE: 16

| | | | | | | | | | | | | | | | |
|---|---|---|---|---|---|---|---|---|---|---|---|---|---|---|---|
| Met | Ala | Phe | Phe | Asp | Met | Pro | Leu | Glu | Glu | Leu | Lys | Lys | Tyr | Arg | Pro |
| 1 | | | | 5 | | | | | 10 | | | | | 15 | |
| Glu | Arg | Tyr | Glu | Glu | Lys | Asp | Phe | Asp | Glu | Phe | Trp | Arg | Glu | Thr | Leu |
| | | | 20 | | | | | 25 | | | | | 30 | | |
| Lys | Glu | Ser | Glu | Gly | Phe | Pro | Leu | Asp | Pro | Val | Phe | Glu | Lys | Val | Asp |
| | | 35 | | | | | 40 | | | | | 45 | | | |
| Phe | His | Leu | Lys | Thr | Val | Glu | Thr | Tyr | Asp | Val | Thr | Phe | Ser | Gly | Tyr |
| | 50 | | | | | 55 | | | | | 60 | | | | |
| Arg | Gly | Gln | Arg | Ile | Lys | Gly | Trp | Leu | Leu | Val | Pro | Lys | Leu | Ala | Glu |
| 65 | | | | 70 | | | | | 75 | | | | | 80 | |
| Glu | Lys | Leu | Pro | Cys | Val | Val | Gln | Tyr | Ile | Gly | Tyr | Asn | Gly | Gly | Arg |
| | | | | 85 | | | | | 90 | | | | | 95 | |
| Gly | Phe | Pro | His | Asp | Trp | Leu | Phe | Trp | Pro | Ser | Met | Gly | Tyr | Ile | Cys |
| | | | 100 | | | | | 105 | | | | | 110 | | |
| Phe | Val | Met | Asp | Thr | Arg | Gly | Gln | Gly | Ser | Gly | Trp | Met | Lys | Gly | Asp |
| | | 115 | | | | | 120 | | | | | 125 | | | |
| Thr | Pro | Asp | Tyr | Pro | Glu | Gly | Pro | Val | Asp | Pro | Gln | Tyr | Pro | Gly | Phe |
| | 130 | | | | | 135 | | | | | 140 | | | | |
| Met | Thr | Arg | Gly | Ile | Leu | Asp | Pro | Gly | Thr | Tyr | Tyr | Tyr | Arg | Arg | Val |
| 145 | | | | 150 | | | | | 155 | | | | | 160 | |
| Phe | Val | Asp | Ala | Val | Arg | Ala | Val | Glu | Ala | Ala | Ile | Ser | Phe | Pro | Arg |
| | | | | 165 | | | | | 170 | | | | | 175 | |
| Val | Asp | Ser | Arg | Lys | Val | Val | Val | Ala | Gly | Ser | Gln | Gly | Gly | Gly | Gly |
| | | | 180 | | | | | 185 | | | | | 190 | | |
| Ile | Ala | Leu | Ala | Val | Ser | Ala | Leu | Ser | Asn | Arg | Val | Lys | Ala | Leu | Leu |
| | | 195 | | | | | 200 | | | | | 205 | | | |
| Cys | Asp | Val | Pro | Phe | Leu | Cys | His | Phe | Arg | Arg | Ala | Val | Gln | Leu | Val |
| | 210 | | | | | 215 | | | | | 220 | | | | |
| Asp | Thr | His | Pro | Tyr | Val | Glu | Ile | Thr | Asn | Phe | Leu | Lys | Thr | His | Arg |
| 225 | | | | 230 | | | | | 235 | | | | | 240 | |
| Asp | Lys | Glu | Glu | Ile | Val | Phe | Arg | Thr | Leu | Ser | Tyr | Phe | Asp | Gly | Val |
| | | | | 245 | | | | | 250 | | | | | 255 | |
| Asn | Phe | Ala | Ala | Arg | Ala | Lys | Val | Pro | Ala | Leu | Phe | Ser | Val | Gly | Leu |
| | | | 260 | | | | | 265 | | | | | 270 | | |
| Met | Asp | Thr | Ile | Cys | Pro | Pro | Ser | Thr | Val | Phe | Ala | Ala | Tyr | Asn | His |
| | | 275 | | | | | 280 | | | | | 285 | | | |
| Tyr | Ala | Gly | Pro | Lys | Glu | Ile | Arg | Ile | Tyr | Pro | Tyr | Asn | Asn | His | Glu |
| | 290 | | | | | 295 | | | | | 300 | | | | |
| Gly | Gly | Gly | Ser | Phe | Gln | Ala | Ile | Glu | Gln | Val | Lys | Phe | Leu | Lys | Arg |
| 305 | | | | 310 | | | | | 315 | | | | | 320 | |
| Leu | Phe | Glu | Glu | Gly | | | | | | | | | | | |
| | | | | 325 | | | | | | | | | | | |

<210> SEQ ID NO 17
<211> LENGTH: 978
<212> TYPE: DNA
<213> ORGANISM: Thermotoga maritima
<220> FEATURE:
<221> NAME/KEY: misc_feature
<222> LOCATION: (1)..(978)
<223> OTHER INFORMATION: Thermotoga maritima MSB8

<400> SEQUENCE: 17

```
atggccttct tcgatttacc actcgaagaa ctgaagaaat atcgtccaga gcggtacgaa      60
gagaaagact tcgatgagtt ctgggaagag acactcgcag agagcgaaaa gttcccctta     120
gaccccgtct tcgagaggat ggagtctcac ctcaaaacag tcgaagcgta cgatgtcacc     180
ttctccggat acaggggaca gaggatcaaa gggtggctcc ttgttccaaa actggaagaa     240
gaaaaacttc cctgcgttgt gcagtacata ggatacaacg gtggaagagg attccctcac     300
gactggctgt tctggccttc tatgggttac atatgtttcg tcatggatac tcgaggtcag     360
ggaagcggct ggctgaaagg agacacaccg gattaccctg agggtcccgt tgaccctcag     420
tatccaggat tcatgacaag aggaatactg gatcccagaa cttactacta cagacgagtc     480
ttcacggacg ctgtcagagc cgttgaagct gctgcttctt ttcctcaggt agatcaagaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagagca     660
gtacagcttg tggatacgca tccatacgcg gagatcacga actttctaaa gacccacaga     720
gacaaggaag aaatcgtgtt caggactctt tcctatttcg atggagtgaa cttcgcagcc     780
agagcgaaga tccctgcgct gttttctgtg gtctcatgg acaacatttg tcctccttca     840
acggttttcg ctgcctacaa ttactacgct ggaccgaagg aaatcagaat ctatccgtac     900
aacaaccacg agggaggagg ctctttccaa gcggttgaac aggtgaaatt cttgaaaaaa     960
ctatttgaga aaggctaa                                                   978
```

<210> SEQ ID NO 18
<211> LENGTH: 325
<212> TYPE: PRT
<213> ORGANISM: Thermotoga maritima
<220> FEATURE:
<221> NAME/KEY: MISC_FEATURE
<222> LOCATION: (1)..(325)
<223> OTHER INFORMATION: Thermotoga maritima MSB8

<400> SEQUENCE: 18

```
Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
```

```
                   165                 170                 175
Val Asp Gln Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                    245                 250                 255

Asn Phe Ala Ala Arg Ala Lys Ile Pro Ala Leu Phe Ser Val Gly Leu
                260                 265                 270

Met Asp Asn Ile Cys Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 19
<211> LENGTH: 963
<212> TYPE: DNA
<213> ORGANISM: Thermoanaerobacterium sp.

<400> SEQUENCE: 19
atgggacttt tcgacatgcc attacaaaaa cttagagaat acactggtac aaatccatgc      60
cctgaagatt tcgatgagta ttggaatagg gctttagatg agatgaggtc agttgatcct     120
aaaattgaat tgaaagaaag tagctttcaa gtatcctttg cagaatgcta tgacttgtac     180
tttacaggtg ttcgtggtgc cagaattcat gcaaagtata taaaacctaa gacagaaggg     240
aaacatccag cgttgataag atttcatgga tattcgtcaa attcaggcga ctggaacgac     300
aaattaaatt acgtggcggc aggcttcacc gttgtggcta tggatgtaag aggtcaagga     360
gggcagtctc aagatgttgg cggtgtaact gggaatactt taaatgggca tattataaga     420
gggctagacg atgatgctga taatatgctt tcaggcata ttttcttaga cactgcccaa     480
ttggctggaa tagttatgaa catgccagaa gttgatgaag atagagtggg agtcatggga     540
ccttctcaag gcggagggct gtcgttggcg tgtgctgcat ggagccaagg gtacgcaaa      600 gtagtatctg aatatccttt tttatctgac tacaagagag tttgggactt agaccttgca     660
aaaaacgcct atcaagagat tacggactat ttcaggcttt ttgacccaag gcatgaaagg     720
gagaatgagg tatttacaaa gcttggatat atagacgtta aaaaccttgc gaaaaggata     780
aaaggcgatg tcttaatgtg cgttgggctt atggaccaag tatgtccgcc atcaactgtt     840
tttgcagcct acaacaacat acagtcaaaa aaagatataa aagtgtatcc tgattatgga     900
catgaaccta tgagaggatt tggagattta gcgatgcagt ttatgttgga actatattca     960
taa                                                                     963

<210> SEQ ID NO 20
<211> LENGTH: 320
<212> TYPE: PRT
<213> ORGANISM: Thermoanaerobacterium sp.
```

-continued

<400> SEQUENCE: 20

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Val Gly Gly
        115                 120                 125

Val Thr Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 21
<211> LENGTH: 1023
<212> TYPE: DNA
<213> ORGANISM: Bacillus sp.
<220> FEATURE:
<221> NAME/KEY: misc_feature
<222> LOCATION: (1)..(1023)
<223> OTHER INFORMATION: Bacillus sp. NRRL B-14911

<400> SEQUENCE: 21
atgaggacgg ttcctgctcc tgttttttg gagaggagtg gggagatgaa ccttttgat      60 atgccccttg aggagctgca gcattacaag cctgcccaga ccaggcagga tgattttgag    120
tcattctgga aaaagcggat tgaggagaac agtcaatatc cgctgaatat agaagtaatg    180

```
gagcgggttt atccggttcc gggagtgaga gtatatgata tttattttga cgggttccgg    240
aattcccgca tccatggggt gtatgttact ccagaaactc cgggagcgga cactcctgcg    300
gcagtgattt ttcacggcta taactggaac acgctgcagc cgcattacag cttcaagcac    360
gtgattcagg ggattcctgt actgatggtg gaggtgcggg acaaaatct cttgtctcca    420 gatagaaatc attatgggaa tggaggtccg ggaggctgga tgacactcgg cgtgatggat    480
cccgatcaat attattacag cctggtatat atggactgct tccgcagcat tgatgctgtc    540
agggaactgt cgaggaagag aagtgtgttt gtggaaggcg aagccaggg aggtgcactg     600 gcgattgccg cagccgccct gcaggatgac atcctgcttg cactcgccga catcccttt     660 ctcacccatt tcaagcgttc cgtggagctt cctcggatg accgtatca ggagatttcc      720 cactacttca aagttcatga tcctcttcat caaacggaag agcaggtata tcagacgctc    780
agctatgtgg actgcatgaa catggccagc atggttgaat gtccagtcct tctttcagcc    840
ggtctggaag acatcgtttg tccccgtcc agtgcatttg cactgttcaa ccatctcggc     900
gggccaaaag aaatacgggc ctatccggaa tacgcccatg aagtaccggc tgtccatgaa    960
gaggaaaagc tgaagtttat atcttcaagg ctaaaaata gagaaagag gtgccggcca     1020 tga                                                                 1023
```

<210> SEQ ID NO 22
<211> LENGTH: 340
<212> TYPE: PRT
<213> ORGANISM: Bacillus sp.
<220> FEATURE:
<221> NAME/KEY: MISC_FEATURE
<222> LOCATION: (1)..(340)
<223> OTHER INFORMATION: Bacillus sp. NRR1 B-14911

<400> SEQUENCE: 22

```
Met Arg Thr Val Pro Ala Pro Val Phe Leu Glu Arg Ser Gly Glu Met
1               5                   10                  15

Asn Leu Phe Asp Met Pro Leu Glu Glu Leu Gln His Tyr Lys Pro Ala
            20                  25                  30

Gln Thr Arg Gln Asp Asp Phe Glu Ser Phe Trp Lys Lys Arg Ile Glu
        35                  40                  45

Glu Asn Ser Gln Tyr Pro Leu Asn Ile Glu Val Met Glu Arg Val Tyr
    50                  55                  60

Pro Val Pro Gly Val Arg Val Tyr Asp Ile Tyr Phe Asp Gly Phe Arg
65                  70                  75                  80

Asn Ser Arg Ile His Gly Val Tyr Val Thr Pro Glu Thr Pro Gly Ala
                85                  90                  95

Asp Thr Pro Ala Ala Val Ile Phe His Gly Tyr Asn Trp Asn Thr Leu
            100                 105                 110

Gln Pro His Tyr Ser Phe Lys His Val Ile Gln Gly Ile Pro Val Leu
        115                 120                 125

Met Val Glu Val Arg Gly Gln Asn Leu Leu Ser Pro Asp Arg Asn His
    130                 135                 140

Tyr Gly Asn Gly Gly Pro Gly Gly Trp Met Thr Leu Gly Val Met Asp
145                 150                 155                 160

Pro Asp Gln Tyr Tyr Tyr Ser Leu Val Tyr Met Asp Cys Phe Arg Ser
                165                 170                 175

Ile Asp Ala Val Arg Glu Leu Ser Arg Lys Arg Ser Val Phe Val Glu
            180                 185                 190

Gly Gly Ser Gln Gly Gly Ala Leu Ala Ile Ala Ala Ala Leu Gln
        195                 200                 205
```

Asp Asp Ile Leu Leu Ala Leu Ala Asp Ile Pro Phe Leu Thr His Phe
        210                 215                 220
Lys Arg Ser Val Glu Leu Ser Ser Asp Gly Pro Tyr Gln Glu Ile Ser
225                 230                 235                 240
His Tyr Phe Lys Val His Asp Pro Leu His Gln Thr Glu Glu Gln Val
                245                 250                 255
Tyr Gln Thr Leu Ser Tyr Val Asp Cys Met Asn Met Ala Ser Met Val
            260                 265                 270
Glu Cys Pro Val Leu Leu Ser Ala Gly Leu Glu Asp Ile Val Cys Pro
        275                 280                 285
Pro Ser Ser Ala Phe Ala Leu Phe Asn His Leu Gly Gly Pro Lys Glu
    290                 295                 300
Ile Arg Ala Tyr Pro Glu Tyr Ala His Glu Val Pro Ala Val His Glu
305                 310                 315                 320
Glu Glu Lys Leu Lys Phe Ile Ser Ser Arg Leu Lys Asn Arg Glu Lys
                325                 330                 335
Arg Cys Arg Pro
            340

<210> SEQ ID NO 23
<211> LENGTH: 960
<212> TYPE: DNA
<213> ORGANISM: Bacillus halodurans
<220> FEATURE:
<221> NAME/KEY: misc_feature
<222> LOCATION: (1)..(960)
<223> OTHER INFORMATION: Bacillus halodurans C-125

<400> SEQUENCE: 23
ttagagatca gataaaaatt gaaaaatccg atcacgatgg cctggcaaat cttcgtgagc      60
aaagtctgga tataactcga tacttttgt cgtcgtgagt ttgttataca tggcaaattg     120
tgtagacggc gggcaaaccg tatccattaa cccaacagca gtaagacttc tccctttac     180
gagtggagca agatgctgaa tatcaatata gcctagcttc gtaaagattt cagcctcacg     240
tcggtgctgt ggatcaaagc gacgaaaata cgtttgcaat tcgtcataag ctttctcggc     300
taaatccatc tcccatacgc gttggtaatc gctaaggaaa ggataaacag gagctacctt     360
tttaattttc ggttccaaag ccgcacaagc aatcgctaag gcccctcctt gtgaccaacc     420
tgtcactgcc acgcgctctt catcgacttc aggaaggttc atcacaatgt tggcaagctg     480
agccgtatca gaaacacat gacgaacaa taattgatca gcattatcat cgagtccgcg     540
tattatatga ccggaatgag tattcccctt cacgcctcct gtgtcttcag acaagcctcc     600
ttgcccgcga acgtccattg caagaacaga atatccgagg gctgcgtaat gaagtaaacc     660
cgtccattcc cccgcattca tcgtatatcc gtgaaaatga ataaccgccg ggtgtgtccc     720
gctcgtgtgt cttgggcgca cgtattttgc gtgaattcta gcaccctaa cccctgtaaa     780
atataggtgg aagcattctg catacgtggt ttgaaaatca ctcggtatga gctctacgtt     840
tggattacc tttctcatct cttgtaaagc acgatccaa tactcagtaa agtcatctgg     900
ctttggatta cgtcccatgt actctttaa ttcggttaac ggcatgtcta ttagtggcat     960

<210> SEQ ID NO 24
<211> LENGTH: 319
<212> TYPE: PRT
<213> ORGANISM: Bacillus halodurans
<220> FEATURE:
<221> NAME/KEY: MISC_FEATURE
<222> LOCATION: (1)..(319)

<223> OTHER INFORMATION: Bacillus halodurans C-125

<400> SEQUENCE: 24

```
Met Pro Leu Ile Asp Met Pro Leu Thr Glu Leu Lys Glu Tyr Met Gly
1               5                   10                  15
Arg Asn Pro Lys Pro Asp Asp Phe Thr Glu Tyr Trp Asp Arg Ala Leu
            20                  25                  30
Gln Glu Met Arg Lys Val Asn Pro Asn Val Glu Leu Ile Pro Ser Asp
        35                  40                  45
Phe Gln Thr Thr Tyr Ala Glu Cys Phe His Leu Tyr Phe Thr Gly Val
    50                  55                  60
Arg Gly Ala Arg Ile His Ala Lys Tyr Val Arg Pro Arg His Thr Ser
65                  70                  75                  80
Gly Thr His Pro Ala Val Ile His Phe His Gly Tyr Thr Met Asn Ala
                85                  90                  95
Gly Glu Trp Thr Gly Leu Leu His Tyr Ala Ala Leu Gly Tyr Ser Val
            100                 105                 110
Leu Ala Met Asp Val Arg Gly Gln Gly Gly Leu Ser Glu Asp Thr Gly
        115                 120                 125
Gly Val Lys Gly Asn Thr His Ser Gly His Ile Ile Arg Gly Leu Asp
    130                 135                 140
Asp Asn Ala Asp Gln Leu Leu Phe Arg His Val Phe Leu Asp Thr Ala
145                 150                 155                 160
Gln Leu Ala Asn Ile Val Met Asn Leu Pro Glu Val Asp Glu Glu Arg
                165                 170                 175
Val Ala Val Thr Gly Trp Ser Gln Gly Gly Ala Leu Ala Ile Ala Cys
            180                 185                 190
Ala Ala Leu Glu Pro Lys Ile Lys Lys Val Ala Pro Val Tyr Pro Phe
        195                 200                 205
Leu Ser Asp Tyr Gln Arg Val Trp Glu Met Asp Leu Ala Glu Lys Ala
    210                 215                 220
Tyr Asp Glu Leu Gln Thr Tyr Phe Arg Arg Phe Asp Pro Gln His Arg
225                 230                 235                 240
Arg Glu Ala Glu Ile Phe Thr Lys Leu Gly Tyr Ile Asp Ile Gln His
                245                 250                 255
Leu Ala Pro Leu Val Lys Gly Val Leu Leu Ala Val Gly Leu Met
            260                 265                 270
Asp Thr Val Cys Pro Pro Ser Thr Gln Phe Ala Met Tyr Asn Lys Leu
        275                 280                 285
Thr Thr Thr Lys Ser Ile Glu Leu Tyr Pro Asp Phe Ala His Glu Asp
    290                 295                 300
Leu Pro Gly His Arg Asp Arg Ile Phe Gln Phe Leu Ser Asp Leu
305                 310                 315
```

<210> SEQ ID NO 25
<211> LENGTH: 954
<212> TYPE: DNA
<213> ORGANISM: Bacillus clausii
<220> FEATURE:
<221> NAME/KEY: misc_feature
<222> LOCATION: (1)..(954)
<223> OTHER INFORMATION: Bacillus clausii KSM-K16

<400> SEQUENCE: 25

```
atgccattag tcgatatgcc gttgcgcgag ttgttagctt atgaaggaat aaaccctaaa        60
ccagcagatt ttgaccaata ctggaaccgg gccaaaacgg aaattgaagc gattgatccc       120
```

-continued

```
gaagtcactc tagtcgaatc ttctttccag tgttcgtttg caaactgtta ccatttctat    180
tatcgaagcg ctggaaatgc aaaaatccat gcgaaatacg tacagccaaa agcaggggag    240
aagacgccag cagtttttat gttccatggg tatgggggc gttcagccga atggagcagc    300
ttgttaaatt atgtagcggc gggttttct gttttctata tggacgtgcg tggacaaggt    360
ggaacttcag aggatcctgg gggcgtaagg gggaatacat ataggggcca cattattcgc    420
ggcctcgatg ccgggccaga cgcactttt taccgcagcg ttttcttgga caccgtccaa    480
ttggttcgtg ctgctaaaac attgcctcac atcgataaaa cacggcttat ggccacaggg    540
tggtcgcaag ggggcgcctt aacgcttgcc tgtgctgccc ttgttcctga atcaagcgt    600 cttgctccag tatcccgtt tttaagcgat acaagcgag tgtggcaaat ggatttagcg    660
gttcgttcgt ataagaatt ggctgattat ttccgttcat acgatccgca acataaacgc    720
catggcgaaa ttttgaacg ccttggctac atcgatgtcc agcatcttgc tgaccggatt    780
caaggagatg tcctaatggg agttggttta atggatacaa aatgcccgcc gtctacccaa    840
tttgctgctt ataataaaat aaaggctaaa aaatcgtatg agctctatcc tgattttggc    900
catgagcacc ttccaggaat gaacgatcat attttcgct ttttcactag ttga    954
```

```
<210> SEQ ID NO 26
<211> LENGTH: 317
<212> TYPE: PRT
<213> ORGANISM: Bacillus clausii
<220> FEATURE:
<221> NAME/KEY: MISC_FEATURE
<222> LOCATION: (1)..(317)
<223> OTHER INFORMATION: Bacillus clausii KSM-K16

<400> SEQUENCE: 26
```

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr

-continued

```
            210                 215                 220
Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
                260                 265                 270

Thr Glu Cys Pro Pro Ser Thr Gln Phe Ala Ala Tyr Asn Lys Ile Lys
            275                 280                 285

Ala Lys Lys Ser Tyr Glu Leu Tyr Pro Asp Phe Gly His Glu His Leu
        290                 295                 300

Pro Gly Met Asn Asp His Ile Phe Arg Phe Phe Thr Ser
305                 310                 315
```

PRODUCTION OF PERACIDS USING AN ENZYME HAVING PERHYDROLYSIS ACTIVITY

This application is a DIV of U.S. patent application Ser. No. 11/638,635, filed Dec. 12, 2006 which claims the benefit of U.S. Provisional Application No. 60/750,092, filed Dec. 13, 2005, and U.S. Provisional Application No. 60/853,065, filed Oct. 20, 2006.

FIELD OF THE INVENTION

This invention relates to the field of peracid biosynthesis and in situ enzyme catalysis. Specifically, a process is provided to produce peracids using the perhydrolysis activity of certain enzymes identified as having cephalosporin C deacetylase activity. The enzymatic process produces percarboxylic acid from carboxylic acid ester substrates.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (U.S. Pat. Nos. 6,545,047; 6,183,807; 6,518, 307; US 20030026846; and U.S. Pat. No. 5,683,724). Peracids have also been reported to be useful in preparing bleaching compositions for laundry detergent applications (U.S. Pat. Nos. 3,974,082; 5,296,161; and 5,364,554).

Peracids can be prepared by the chemical reaction of a carboxylic acid and hydrogen peroxide (see *Organic Peroxides*, Daniel Swern, ed., Vol. 1, pp 313-516; Wiley Interscience, New York). The reaction is usually catalyzed by a strong inorganic acid, such as concentrated sulfuric acid. The reaction of hydrogen peroxide with a carboxylic acid is an equilibrium reaction, and the production of peracid is favored by the use of an excess concentration of peroxide and/or carboxylic acid, or by the removal of water. There are several disadvantages to the chemical reaction for peracid production: a) the high concentration of carboxylic acid used to favor production of peracid can result in an undesirable odor when using the peracid-containing solution, 2) the peracid is oftentimes unstable in solution over time, and the concentration of peracid in the solution decreases during storage prior to use, and 3) the formulation is often strongly acidic due to the use of a concentrated sulfuric acid as catalyst.

One way to overcome the disadvantages of the chemical production of peracids is to employ an enzyme catalyst in place of a strong acid catalyst. The use of an enzyme catalyst allows for the rapid production of peracid at the time of use and/or application, avoiding problems associated with storage of peracid solutions and variations in peracid concentrations over time. The high concentrations of carboxylic acids typically used to produce peracid via the direct chemical reaction with hydrogen peroxide are not required for enzymatic production of peracid, where the enzyme-catalyzed reaction can use a carboxylic acid ester as substrate at a much lower concentration than is typically used in the chemical reaction. The enzyme reaction can be performed across a broad range of pH, dependent on enzyme activity and stability at a given pH, and on the substrate specificity for perhydrolysis at a given pH.

Some esterases, proteases, and lipases have the ability catalyze the hydrolysis of alkyl esters to produce the corresponding carboxylic acids (Formula 1).

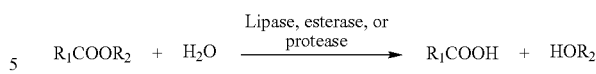

Formula 1

Some esterases, proteases, and lipases also exhibit perhydrolysis activity, catalyzing the synthesis of peracids from alkyl esters (Formula 2).

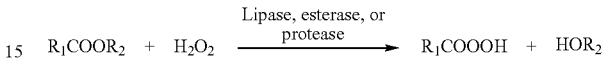

Formula 2

O. Kirk et al. (*Biocatalysis*, 11:65-77 (1994)) investigated the ability of hydrolases (lipases, esterases, and proteases) to catalyze perhydrolysis of acyl substrates with hydrogen peroxide to form peroxycarboxylic acids, and reported that perhydrolysis proceeds with a very low efficiency in aqueous systems. Furthermore, they found that lipases and esterases degraded percarboxylic acid to the corresponding carboxylic acid and hydrogen peroxide. They also found that proteases neither degraded nor catalyzed perhydrolysis of carboxylic acid esters in water. The authors concluded that esterases, lipases and proteases are, in general, not suitable for catalyzing perhydrolysis of simple esters, such as methyl octanoate and trioctanoin, in an aqueous environment.

U.S. Pat. No. 3,974,082 describes the production of bleaching compositions for laundry detergent applications by contacting the material to be bleached with an aqueous solution containing an oxygen releasing inorganic peroxygen compound, an acyl alkyl ester, and an esterase or lipase capable of hydrolyzing the ester.

U.S. Pat. No. 5,364,554 describes an activated oxidant system for in situ generation of peracid in aqueous solution using a protease enzyme, a source of hydrogen peroxide, and an ester substrate that is preferably chemically non-perhydrolyzable. A method of bleaching and a method of forming peracid are also disclosed.

U.S. Pat. No. 5,296,161 describes production of peracid in an aqueous solution comprising one or more specific esterases and lipases, a source of hydrogen peroxide, and a functionalized ester substrate suitable for use in a bleaching composition. However, the concentration of peracid produced was generally insufficient for use in many commercial disinfectant applications.

Most known methods for preparing peracids from the corresponding carboxylic acid esters using enzyme catalysts do not produce and accumulate a peracid at a sufficiently-high concentration to be efficacious for disinfection in a variety of applications. Several protease and lipase combinations have recently been reported to generate peracids (e.g., peracetic acid) in situ at concentrations suitable for use as a disinfectant and/or commercial bleaching agent (see co-owned U.S. patent application Ser. Nos. 11/413,246 and 11/588,523; herein incorporated by reference). However, there remains a need to identify additional perhydrolase catalysts capable of producing peracids in situ.

U.S. Pat. No. 4,444,886 describes a strain of *Bacillus subtilis* (ATCC 31954™) having ester hydrolase activity (described as a "diacetinase") that has high specificity for hydrolyzing glycerol esters having acyl groups having 2 to 8 carbon atoms. U.S. Pat. No. 4,444,886 does not describe, discuss or predict that the ester hydrolase activity of this strain has perhydrolase activity towards carboxylic acid esters, including glycerol esters.

The problem to be solved is to provide a process to enzymatically produce peracids in situ at concentrations suitable for use in a variety of disinfectant applications and/or bleaching applications. Preferably, the substrates used to produce the peracid compositions should be relatively non-toxic and inexpensive, such as carboxylic acid esters, especially mono-, di-, and triacylglycerols, where the acyl group has 1-8 carbon atoms.

SUMMARY OF THE INVENTION

The stated problems have been solved by the discovery that certain enzymes having cephalosporin C deacetylase activity exhibit perhydrolysis activity for converting carboxylic acid esters in the presence of an inorganic source of peroxygen (e.g. hydrogen peroxide) into peracids at concentrations sufficient for use as a disinfectant and/or bleaching agent. The system achieves efficiency by producing the peracid in high concentrations without requiring a high concentration peroxygen.

Specifically, enzymes identified as having cephalosporin C deacetylase activity from *Bacillus subtilis* (ATCC 31954™), an I.M.A.G.E. Consortium [LLNL] cDNA clone (Lennon, et al., *Genomics*, 33:151-152 (1996)) and *B. subtilis* BE1010 were found to have perhydrolysis activity for converting carboxylic acid esters (in the presence of a source of peroxygen) into peracids in situ at concentrations sufficient for use as a disinfectant and/or bleaching agent.

An enzyme providing the perhydrolysis activity from *Bacillus subtilis* ATCC 31954™ was isolated. Amino-terminal sequence analysis identified the enzyme as a cephalosporin C deacetylase ("CAH", a member of the carbohydrate esterase family seven; also referred to as a CE-7 esterase) from *Bacillus subtilis*. The corresponding gene encoding CAH from *Bacillus subtilis* ATCC 31954™ was isolated, sequenced and heterologously expressed in a microbial cell. The deduced amino acid sequence for this enzyme (SEQ ID NO: 2) was determined to have 100% amino acid identity to CAH from *B. subtilis* HS 0133 (Mitsushima et al., *Appl. Environ. Microbiol.*, 61(6): 2224-2229 (1995); U.S. Pat. Nos. 5,528,152; 5,338,676; and Vincent et al., *J. Mol. Biol.* 330:593-606 (2003)).

A second gene encoding a CAH from *Bacillus subtilis* BE1010 was isolated, heterologously expressed, and shown to have significant perhydrolysis activity. The deduced amino acid sequence for this enzyme was determined to have 100% amino acid identity to CAH from *Bacillus subtilis* subsp. *subtilis* strain 168 (SEQ ID NO: 6; Kunst et al., supra). The amino acid sequence of SEQ ID NO: 2 and SEQ ID NO: 6 differ by 4 amino acids. One of skill in the art would therefore expect that other enzymes, (such as other enzymes having CAH activity), having substantially similar structure would also exhibit perhydrolysis activity.

The enzyme catalyst having perhydrolysis activity used in the present process may be in the form of whole cells expressing a CAH, permeabilized whole cells expressing a CAH, one or more cell components of a microbial cell extract comprising a CAH, partially-purified CAH enzyme, and purified CAH enzyme. The enzyme catalyst may be unimmobilized or immobilized, including but not limited to: immobilization in or on an insoluble solid support, covalently attached to a soluble polymer (e.g., low-molecular weight polyethylene glycol (PEG), and immobilized as soluble enzyme in a hollow-fiber cartridge.

In one aspect of the invention, an aqueous enzymatic process for in situ generation of peracids is provided. Said process comprises:

a) providing a set of reaction components, said components comprising:
1) a carboxylic acid ester selected from the group consisting of:
i) esters having the structure

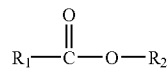

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2-O)_nH$ or $(CH_2CH(CH_3)-O)_nH$ and n=1 to 10; and ii) glycerides having the structure

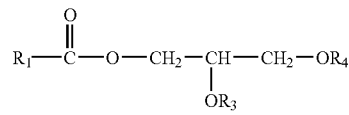

wherein $R_1$=C1 to C7 straight chain or branched chain alkyl optionally substituted with an hydroxyl or a C1 to C4 alkoxy group and $R_3$ and $R_4$ are individually H or $R_1C(O)$;

2) a source of peroxygen; and
3) an enzyme catalyst having perhydrolysis activity, wherein said enzyme catalyst comprises a member selected from group consisting of:
(i) an enzyme having at least 95% amino acid identity to SEQ ID NO: 2 or SEQ ID NO: 6;
(ii) an enzyme having an amino sequence of SEQ ID NO: 2 or SEQ ID NO: 6, or a substantially similar enzyme derived from SEQ ID NO: 2 or SEQ ID NO: 6 by substituting, deleting or adding one or more amino acids in the amino acid sequence; and
(iii) a polypeptide encoded by a nucleic acid sequence that hybridizes to SEQ ID NO:1 or SEQ ID NO:5 under stringent conditions; and b) combining said reaction components under suitable aqueous reaction conditions, wherein said conditions comprise a pH range of about 2 to about 9, whereby a peroxycarboxylic acid is produced.

A further process for producing peroxycarboxylic acid from a carboxylic acid ester is described, said process comprises a) providing a set of reaction components, said components comprising:
1) a carboxylic acid ester selected from the group consisting of:
i) esters having the structure

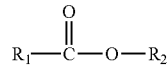

wherein $R_1$=C1 to C7 straight chain or branched chain alkyl optionally substituted with an hydroxyl or a C1 to C4 alkoxy group and $R_2$=C1 to C10 straight chain or branched chain alkyl group, $(CH_2CH_2\text{—}O)_nH$ or $(CH_2CH(CH_3)\text{—}O)_nH$ and n=1 to 10; and ii) glycerides having the structure

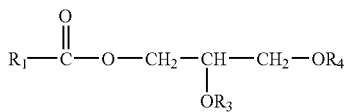

wherein $R_1$=C1 to C7 straight chain or branched chain alkyl optionally substituted with an hydroxyl or a C1 to C4 alkoxy group and $R_3$ and $R_4$ are individually H or $R_1C(O)$;

2) a source of peroxygen; and 3) at least one enzyme catalyst of *Bacillus subtilis* ATCC 31954 having perhydrolysis activity; and b) combining said reaction components under suitable aqueous reaction conditions, wherein said conditions comprise a pH range of about 2 to about 9, whereby a peroxycarboxylic acid is produced at a concentration of at least 200 ppm within about 10 minutes to about 2 hours of combining the reaction components.

In another aspect of the invention, a method is provided to reduce a concentration of a microbial population on a hard surface or inanimate object by contacting the peracid composition produced by the either of the above processes with said hard surface or inanimate object, whereby the concentration of the microbial population is reduced at least 3-log, preferably at least 4-log, more preferably at least 5-log, and most preferably at least 6-log. In a further aspect, the peracid composition produced by the above methods may be optionally diluted to a desired efficacious concentration prior to contacting the surface or inanimate object to be treated.

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e).

SEQ ID NO: 1 is the nucleic acid sequence of the cephalosporin C deacetylase (cah) coding region from *Bacillus subtilis* ATCC 31954™.

SEQ ID NO: 2 is the deduced amino acid sequence of the cephalosporin C deacetylase from *Bacillus subtilis* ATCC 31954™.

SEQ ID NOs: 3 and 4 are primers used to PCR amplify the cephalosporin C deacetylase coding region from *Bacillus sp.*

SEQ ID NO: 5 is the nucleic acid sequence of the cephalosporin C deacetylase coding region from *B. subtilis* subsp. *subtilis* str. 168.

SEQ ID NO: 6 is the deduced amino acid sequence of the cephalosporin C deacetylase from *B. subtilis* subsp. *subtilis* str. 168.

SEQ ID NO: 7 is the nucleic acid sequence of the cephalosporin acetylesterase coding region from *B. subtilis* ATCC 6633.

SEQ ID NO: 8 is the deduced amino acid sequence of the cephalosporin acetylesterase from *B. subtilis* ATCC 6633.

SEQ ID NO: 9 is the nucleic acid sequence of the cephalosporin C deacetylase coding region from *B. licheniformis* ATCC 14580.

SEQ ID NO: 10 is the deduced amino acid sequence of the cephalosporin C deacetylase from *B. licheniformis* ATCC 14580.

SEQ ID NO: 11 is the nucleic acid sequence of the acetyl xylan esterase coding region from *B. pumilus*.

SEQ ID NO: 12 is the deduced amino acid sequence of the acetyl xylan esterase from *B. pumilus*.

SEQ ID NO: 13 is the nucleic acid sequence of the acetyl xylan esterase coding region from *Clostridium thermocellum* ATCC 27405.

SEQ ID NO: 14 is the deduced amino acid sequence of the acetyl xylan esterase from *Clostridium thermocellum* ATCC 27405.

SEQ ID NO: 15 is the nucleic acid sequence of the acetyl xylan esterase coding region from *Thermotoga neapolitana*.

SEQ ID NO: 16 is the deduced amino acid sequence of the acetyl xylan esterase from *Thermotoga neapolitana*.

SEQ ID NO: 17 is the nucleic acid sequence of the acetyl xylan esterase coding region from *Thermotoga maritime* MSB8.

SEQ ID NO: 18 is the deduced amino acid sequence of the acetyl xylan esterase from *Thermotoga maritime* MSB8.

SEQ ID NO: 19 is the nucleic acid sequence of the acetyl xylan esterase coding region from *Thermoanaerobacterium* sp. JW/SL YS485.

SEQ ID NO: 20 is the deduced amino acid sequence of the acetyl xylan esterase from *Thermoanaerobacterium* sp. JW/SL YS485.

SEQ ID NO: 21 is the nucleic acid sequence of the cephalosporin C deacetylase coding region from *Bacillus* sp. NRRL B-14911.

SEQ ID NO: 22 is the deduced amino acid sequence of the cephalosporin C deacetylase from *Bacillus* sp. NRRL B-14911.

SEQ ID NO: 23 is the nucleic acid sequence of the cephalosporin C deacetylase coding region from *Bacillus halodurans* C-125.

SEQ ID NO: 24 is the deduced amino acid sequence of the cephalosporin C deacetylase from *Bacillus halodurans* C-125.

SEQ ID NO: 25 is the nucleic acid sequence of the cephalosporin C deacetylase coding region from *Bacillus clausii* KSM-K16.

SEQ ID NO: 26 is the deduced amino acid sequence of the cephalosporin C deacetylase from *Bacillus clausii* KSM-K16.

DETAILED DESCRIPTION OF THE INVENTION

The stated problems have been solved by the discovery that certain enzymes having cephalosporin C deacetylase (CAH) activity and perhydrolysis activity for converting carboxylic acid ester substrates to peracids can be used to generate concentrations of peracids with high efficiency for disinfection and/or bleaching applications.

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "suitable enzymatic reaction mixture", "components suitable for in situ generation of a peracid", "suitable reaction components", and "suitable aqueous reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multicomponent system wherein one or more of the reaction components remains separated until use. The design of systems for combining multiple active components are known in the art and generally will depend upon the physical form of the individual reaction components. For example, multiple active fluids (liquid-liquid) systems typically use multichamber dispenser bottles or two-phase systems (U.S. Patent Application Pub. No. 2005/0139608; U.S. Pat. Nos. 5,398,846; 5,624,634; 6,391,840; E.P. Patent No. 0807156B1; U.S. Patent Appln. Pub. No. 2005/0008526; and PCT Publication No. WO 00/11713A1) such as found in some bleaching applications wherein the desired bleaching agent is produced upon mixing the reactive fluids. Other forms of multicomponent systems used to generate peracid may include, but are not limited to those designed for one or more solid components or combinations of solid-liquid components, such as powders (e.g., many commercially available bleaching composition, U.S. Pat. No. 5,116,575), multi-layered tablets (U.S. Pat. No. 6,210,639), water dissolvable packets having multiple compartments (U.S. Pat. No. 6,995, 125) and solid agglomerates that react upon the addition of water (U.S. Pat. No. 6,319,888).

As used herein, the term "perhydrolysis" is defined as the reaction of a selected substrate with peroxide to form a peracid. Typically, an inorganic peroxide is reacted with the selected substrate in the presence of a catalyst to produce the peracid. As used herein, the term "chemical perhydrolysis" includes perhydrolysis reactions in which a substrate (a peracid precursor) is combined with a source of hydrogen peroxide wherein peracid is formed in the absence of an enzyme catalyst.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme may be produced by a source strain (i.e. *Bacillus subtilis,* such as *Bacillus subtilis* ATCC 31954™) or may be recombinantly produced in a microbial host cell. As described herein, an enzyme catalyst is provided having perhydrolysis activity towards carboxylic acid esters. In one aspect, the enzyme catalyst comprises an enzyme having at least 95% amino acid identity to SEQ ID NO: 2 or SEQ ID NO:6. In a preferred aspect, the enzyme catalyst comprises the enzyme as represented by SEQ ID NO:2 or SEQ ID NO:6, or a substantially similar enzyme derived from SEQ ID NO: 2 or SEQ ID NO: 6 by substituting, deleting or adding one or more amino acids in the amino acid sequence. In another aspect, the enzyme catalyst comprises a polypeptide encoded by a nucleic acid sequence that hybridizes to SEQ ID NO:1 or SEQ ID NO:5 under stringent conditions. The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

As used herein, the term "*Bacillus subtilis* (ATCC 31954™)" refers to a bacterial cell deposited to the American Type Culture Collection (ATCC) having international depository accession number ATCC 31954™. *Bacillus subtilis* ATCC 31954™ has been reported to have an ester hydrolase ("diacetinase") activity capable of hydrolyzing glycerol esters having 2 to 8 carbon acyl groups, especially diacetin (U.S. Pat. No. 4,444,886; herein incorporated by reference in its entirety). As described herein, an enzyme having significant perhydrolase activity has been isolated from *B. subtilis* ATCC 31954™ and is provided as SEQ ID NO: 2. The amino acid sequence of the isolated enzyme has 100% amino acid identity to the cephalosporin C deacetylase provided by Gen-Bank® Accession No. BAA01729.1.

As used herein, the term "*Bacillus subtilis* BE1010" refers to the strain of *Bacillus subtilis* as reported by Payne and Jackson (*J. Bacteriol.* 173:2278-2282 (1991)). *Bacillus subtilis* BE1010 is a derivative *Bacillus subtilis* subsp. *subtilis* strain BR151 (ATCC 33677™) having a chromosomal deletion in the genes encoding subtilisin and neutral protease. As described herein, an enzyme having significant perhydrolase activity has been isolated from *B. subtilis* BE1010 and is provided as SEQ ID NO: 6. The amino acid sequence of the isolated enzyme has 100% amino acid identity to the cephalosporin C deacetylase reported in *Bacillus subtilis* subsp. *subtilis* strain 168 (Kunst et al., supra).

As used herein, the term "cephalosporin C deacetylase" refers to an enzyme (E.C. 3.1.1.41) that catalyzes the deacetylation of cephalosporins such as cephalosporin C and 7-aminocephalosporanic acid (Mitsushima et al., supra). As described herein, enzymes having 100% amino acid identity to the cephalosporin C deacetylase from *Bacillus subtilis* SHS 0133 (SEQ ID NO: 2; GenBank® Accession No BAA01729.1) or 100% amino acid identity to the cephalosporin C deacetylase from *Bacillus subtilis* subsp. *subtilis* strain 168 (SEQ ID NO: 6) also have significant perhydrolytic activity suitable for producing percarboxylic acids from the present carboxylic acid esters. The present application describes, for the first time, the use of enzymes classified as cephalosporin C deacetylases (E.C. 3.1.1.41) for perhydrolysis. As such, one of skill in the art would expect that enzymes substantially similar in structure to SEQ ID NO: 2 or SEQ ID NO: 6 would also have similar activity. Means to identify substantially similar biological molecules are well known in the art (e.g. sequence alignment protocols, nucleic acid hybridizations, etc.). In one aspect, the enzyme catalyst in the present process comprises a substantially similar enzyme having at least 50%, preferably at least 60%, more preferable at least 70%, even more preferably at least 80%, yet even more preferable at least 90% identity, and most preferably at least 95% amino acid identity, to SEQ ID NO: 2 or SEQ ID NO: 6. The present cephalosporin C deacetylases may be encoded by the cah coding sequence as represented by SEQ ID NO: 1 or SEQ ID NO: 5. In a further embodiment, the perhydrolase catalyst useful in the present process is encoded by a nucleic acid molecule that hybridizes, preferably under stringent conditions, to SEQ ID NO: 1 or SEQ ID NO: 5.

As used herein, an "isolated nucleic acid molecule" and "isolated nucleic acid fragment" will be used interchangeably and refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, "substantially similar" refers to nucleic acid molecules wherein changes in one or more nucleotide bases results in the addition, substitution, or deletion of one or more amino acids, but does not affect the functional properties (i.e. perhydrolytic activity) of the protein encoded by the DNA sequence. As used herein, "substantially similar" also refers to enzymes having amino acid sequences that are least lest 50%, preferably at least 60%, more preferably at least 70%, even more preferably at least 80%, yet even more preferably at least 90%, and most preferably at least 95% to the sequence reported herein wherein the resulting enzyme retains the present functional properties (i.e., perhydrolytic activity). "Substantially similar" may also refer to an enzyme having perhydrolytic activity encoded by nucleic acid molecules that hybridize under stringent conditions to the nucleic acid molecules reported herein (e.g. SEQ ID NO:1 or SEQ ID NO: 5). It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by within the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein. In one embodiment, the present invention includes isolated nucleic acid molecules that hybridize under stringent conditions to nucleic acid molecules encoding.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J., Fritsch, E. F. and Maniatis, T. *Molecular Cloning: A Laboratory Manual,* Third Edition, Cold Spring Harbor Laboratory Press, Cold Spring Harbor (2001) (hereinafter "Maniatis"). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis, supra). For hybridizations with shorter nucleic acids, i.e., oligonucleotides, the position of mismatches becomes more important, and the length of the oligonucleotide determines its specificity (see Maniatis, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.) or the AlignX program of Vector NTI v. 7.0 (Informax, Inc., Bethesda, Md.). Multiple alignment of the sequences can be performed using the Clustal method of alignment (Higgins and Sharp, *CABIOS*, 5:151-153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5 and DIAGONALS SAVED=5.

In one aspect of the present invention, suitable isolated nucleic acid molecules (isolated polynucleotides of the present invention) encode a polypeptide having an amino acid sequence that is at least about 80% identical to the amino acid sequences reported herein. In another aspect, suitable nucleic acid molecules encode amino acid sequences that are at least about 85% identical to the amino acid sequences reported herein. In yet another aspect, suitable nucleic acid molecules encode amino acid sequences that are at least about 90% identical to the amino acid sequences reported herein. In a further aspect, suitable nucleic acid molecules encode amino acid sequences that are at least 95% identical to the amino acid sequences reported herein. In yet a further aspect, suitable isolated nucleic acid molecules encode amino acid sequences that are at least 99% identical to the amino acid sequences reported herein. Suitable nucleic acid molecules of the present invention not only have the above homologies, but also typically encode a polypeptide having about 300 to about 340 amino acids, more preferably about 310 to about 330 amino acids, and most preferably about 318 amino acids.

As used herein, "codon degeneracy" refers to the nature in the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide as set forth in SEQ ID NO: 2 or SEQ ID NO:6. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes, A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or anti-sense orientation.

As used herein, the term "expression" refers to the transcription and stable accumulation of sense (mRNA) or anti-sense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

Accordingly, preferred amino acid fragments are at least about 85% identical to the amino acid sequences herein, more preferred amino acid sequences are at least about 90% identical to the amino acid fragments reported herein, even more preferred amino acid sequences are at least about 95% identical to the amino acid fragments reported herein, and most preferred are nucleic acid molecules that are at least 99% identical to the amino acid molecules reported herein (i.e., SEQ ID NO: 2 or SEQ ID NO: 6).

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 µmol of peracid product per minute at a specified temperature.

As used herein, the term "microbial contaminants" refers to one or more unwanted and/or pathogenic biological agents selected from the group consisting of microorganisms, viruses, prion particles, and mixtures thereof. The present process produces an efficacious concentration of a at least one percarboxylic acid useful to reduce and/or eliminate the presence of the microbial contaminants. In a preferred embodiment, the microbial contaminant is a viable pathogenic microorganism.

As used herein, the term "disinfect" refers to the process of cleansing so as to destroy or prevent the growth of pathogenic microorganisms. As used herein, the term "disinfectant" refers to an agent that disinfects by destroying, neutralizing, or inhibiting the growth of disease-carrying microorganisms. Typically, disinfectants are used to treat inanimate objects or surfaces. As used herein, the term "antiseptic" refers to a chemical agent that inhibits the growth of disease-carrying microorganisms.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is a 3-log reduction, more preferably a 4-log reduction, and most preferably at least a 5-log reduction. In another aspect, the minimum biocidal concentration is a 6-log reduction in viable microbial cells.

As used herein, the terms "peroxygen source" and "source of peroxygen" refer to compounds capable of providing hydrogen peroxide at a concentration of about 10 mM or more when in an aqueous solution including, but not limited to hydrogen peroxide, hydrogen peroxide adducts, perborates, and percarbonates. As described herein, the peroxygen source is capable of providing, upon combining the reaction components, a mixture having a hydrogen peroxide concentration of at least 10 mM. The concentration of the hydrogen peroxide provided by the peroxygen compound in the aqueous reaction mixture is initially at least 10 mM or more upon combining the reaction components. In one embodiment, the hydrogen peroxide concentration in the aqueous reaction mixture is 500 mM or more. In another embodiment, the hydrogen peroxide concentration in the aqueous reaction mixture is 1000 mM or more. In yet another embodiment, the hydrogen peroxide concentration in the aqueous reaction mixture is 2500 mM or more. The molar ratio of the hydrogen peroxide to enzyme substrate, e.g. triglyceride, ($H_2O_2$:substrate) in the aqueous reaction mixture may be from about 0.002 to 20, preferably about 0.1 to 10, and most preferably about 0.5 to 5.

Suitable Reaction Conditions for the Enzyme-catalyzed Preparation of Peracids from Carboxylic Acid Esters and Hydrogen Peroxide In one aspect of the invention, a process is provided to produce an aqueous mixture comprising a peracid by reacting carboxylic acid esters and an inorganic peroxide, not limited to hydrogen peroxide, sodium perborate or sodium percarbonate, in the presence of a Bacillus sp. (e.g. Bacillus subtilis ATCC 31954™, Bacillus subtilis BE1010, Bacillus subtilis subsp. subtilis strain 168, etc.) derived enzyme catalyst having perhydrolysis activity. In one embodiment, the enzyme catalyst comprises an enzyme substantially similar to SEQ ID NO: 2 or SEQ ID NO: 6. In another embodiment, the substantially similar enzyme has at least 95% amino acid identity to SEQ ID NO: 2 or SEQ ID NO: 6 or is encoded by a nucleic acid molecule that hybridizes to SEQ ID NO: 1 or SEQ ID NO: 5 under stringent hybridization conditions, or comprises one or more amino acid additions, substitutions, or deletions so long as the resulting enzyme retains perhydrolysis activity.

Suitable carboxylic acid esters have a formula selected from the group consisting of:

a) esters of the formula

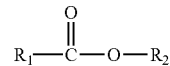

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2\text{—}O)_n H$ or $(CH_2CH(CH_3)\text{—}O)_n H$ and n=1 to 10; and a) glycerides of the formula

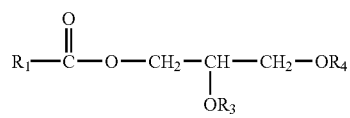

wherein $R_1$=C1 to C7 straight chain or branched chain alkyl optionally substituted with an hydroxyl or a C1 to C4 alkoxy group and $R_3$ and $R_4$ are individually H or $R_1C(O)$.

In one aspect, the carboxylic acid ester is selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol), and mixtures thereof. In another aspect, the carboxylic acid ester substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the carboxylic acid ester substrates are selected from the group consisting of diacetin, triacetin, ethyl acetate, and ethyl lactate.

The carboxylic acid ester is present in the reaction mixture at a concentration sufficient to produce the desired concentration of peracid upon enzyme-catalyzed perhydrolysis. The carboxylic acid ester need not be completely soluble in the reaction mixture, but has sufficient solubility to permit conversion of the ester by the perhydrolase catalyst to the corresponding peracid. The carboxylic acid ester is present in the reaction mixture at a concentration of 0.05 wt % to 40 wt % of the reaction mixture, preferably at a concentration of 0.1 wt % to 20 wt % of the reaction mixture, and more preferably at a concentration of 0.5 wt % to 10 wt % of the reaction mixture.

The peroxygen source may include, but is not limited to, hydrogen peroxide, perborate salts and percarbonate salts. The concentration of peroxygen compound in the reaction mixture may range from 0.033 wt % to about 50 wt %, preferably from 1 wt % to about 40 wt %, more preferably from 2 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction mixture. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM. In a preferred embodiment, the enzyme catalyst lacks significant catalase activity or is engineered to decrease or eliminate catalase activity. In a further embodiment, the catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis.

The concentration of the catalyst in the aqueous reaction mixture depends on the specific catalytic activity of the catalyst, and is chosen to obtain the desired rate of reaction. The weight of catalyst in perhydrolysis reactions typically ranges from 0.0005 mg to 10 mg per mL of total reaction volume, preferably from 0.010 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana-Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peracid generated by the combination of chemical perhydrolysis and enzymatic perhydrolysis of the carboxylic acid ester is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate perhydrolase catalyst to the reaction mixture.

The concentration of peracid generated (e.g. peracetic acid) by the perhydrolysis of at least one carboxylic acid ester is at least about 20 ppm, preferably at least about 200 ppm peracid, preferably at least about 1000 ppm peracid, most preferably at least about 2000 ppm peracid within 10 minutes, preferably within 5 minutes, of initiating the perhydrolysis reaction. The product mixture comprising the peracid may be optionally diluted with water, or a solution predominantly comprised of water, to produce a mixture with the desired lower concentration of peracid. In one aspect, the reaction time required to produce the desired concentration of peracid is not greater than about two hours, preferably not greater than about 30 minutes, more preferably not greater than about 10 minutes, and most preferably in about 5 minutes or less. In other aspects, a hard surface or inanimate object contaminated with a concentration of a microbial population is contacted with the peracid formed in accordance with the processes described herein within about 5 minutes to about 168 hours of combining said reaction components, or within about 5 minutes to about 48 hours, or within about 5 minutes to 2 hours of combining said reaction components, or any such time interval therein.

The temperature of the reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C.

The pH of the final reaction mixture containing peracid is from about 2 to about 9, preferably from about 3 to about 8, more preferably from about 4 to about 7, even more preferably about 4 to about 6.5, and yet even more preferably about 5 to about 6.5. In one embodiment, the pH of the reaction mixture is acidic (pH<7). The pH of the reaction, and of the final reaction mixture, may be controlled by the addition of a suitable buffer, including, but not limited to phosphate, pyrophosphate, bicarbonate, acetate, or citrate. The concentration of buffer is typically from 0.1 mM to 1.0 M, preferably from 1 mM to 300 mM, most preferably from 10 mM to 50 mM.

In another aspect, the enzymatic perhydrolysis product may contain additional components that provide desirable functionality. These additional components include, but are not limited to detergent builders, emulsifiers, surfactants, corrosion inhibitors, enzyme stabilizers, and peroxide stabilizers (e.g., metal ion chelating agents). Many of the additional components are well known in the detergent industry (see for example U.S. Pat. No. 5,932,532; hereby incorporated by reference). Examples of emulsifiers include polyvinyl alcohol or polyvinylpyrrolidine. Examples of surfactants, including a) non-ionic surfactants such as block copolymers of ethylene oxide or propylene oxide, ethoxylated or propoxylated linear and branched primary and secondary alcohols, and aliphatic phosphine oxides b) cationic surfactants such as such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, and alkybetaines. Additional components may include fragrances, dyes, stabilizers of hydrogen peroxide (e.g., 1-hydroxyethylidene-1,1-diphosphonic acid (Dequest 2010, Solutia Inc., St. Louis, Mo.)), stabilizers of enzyme activity (e.g., polyethyleneglycol (PEG)), detergent builders and metal chelators (e.g., ethylenediaminetetraacetic acid (EDTA)).

In Situ Production of Peracids Using a Perhydrolase Catalyst

The present method produces industrially-useful, efficacious concentrations of peracids in situ under aqueous reaction conditions using the perhydrolase activity of an enzyme having cephalosporin C deacetylase activity. As described herein, the genes encoding said enzymes (e.g. enzymes with amino acid sequences SEQ ID NO: 2, SEQ ID NO:6, or substantially similar amino acid sequence) isolated from a *B. subtilis* strain (e.g., *Bacillus subtilis* ATCC 31954™, *Bacillus subtilis* BE1010) have been heterologously expressed in a microbial host cell. Specifically, a perhydrolase was isolated from *Bacillus subtilis* ATCC 31954™. This perhydrolase has 100% amino acid identity to the cephalosporin C deacetylase reported in *Bacillus subtilis* SHS 0133 (Mitshushima et al., supra).

The coding sequence of another perhydrolase gene was isolated from *Bacillus subtilis* BE1010 and heterologously expressed in a microbial host cell (SEQ ID NO: 5; Payne and Jackson, *J. Bacteriol.* 173:2278-2282 (1991)). The amino acid sequence of the perhydrolase from *B. subtilis* BE1010 (SEQ ID NO: 6) has 100% amino acid identity to the cephalosporin C deacetylase reported in *Bacillus subtilis* subsp. *subtilis* strain 168 (Kunst et al., supra; WO99/03984).

The peracids produced are quite reactive and generally decrease in concentration over time. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to the use of multicompartment chambered dispensers (U.S. Pat. No. 4,585,150) and at the time of use physically combining the perhydrolase catalyst with the present substrates to initiate the aqueous enzymatic perhydrolysis reaction. The perhydrolase catalyst may optionally be immobilized within the body of reaction chamber or separated (e.g. filtered, etc.) from the reaction product comprising the peracid prior to contacting the surface and/or object targeted for treatment. The perhydrolase catalyst may be in a liquid matrix or in a solid form (i.e. powdered, tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis.

HPLC Assay Method for Determining the Concentration of Peracid and Hydrogen Peroxide.

A variety of analytical methods can be used in the present method to analyze the reactants and products including, but not limited to titration, high performance liquid chromatography (HPLC), gas chromatography (GC), mass spectroscopy (MS), capillary electrophoresis (CE), the analytical procedure described by U. Karst et al., (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to viable plate counts, direct microscopic counts, dry weight, turbidity measurements, absorbance, and bioluminescence (see, for example Brock, Semour S., *Disinfection, Sterilization, and Preservation,* 5$^{th}$ edition, Lippincott Williams & Wilkins, Philadelphia, Pa., USA; 2001).

Uses of Enzymatically-Prepared Peracid Compositions

The enzyme catalyst-generated peracid produced according to the present methods can be used in a variety of hard surface/inanimate object applications for reduction of concentrations of microbial, fungal, prion-related, and viral contamination, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peracids may be used in formulations designed to inactivate prions (e.g. certain proteases) to additionally provide biocidal activity. In a preferred aspect, the present peracid compositions are particularly useful as a cleaning and disinfecting agent for non-autoclavable medical instruments and food packaging equipment. As the peracid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peracid may be incorporated into a product whose final form is a powder, liquid, gel, film, solid or aerosol. The enzyme-generated peracid may be diluted to a concentration that still provides an efficacious decontamination.

The compositions comprising an efficacious concentration of peracid can be used to clean and disinfect surfaces and/or objects contaminated (or suspected of being contaminated) with pathogenic microbial contaminants by contacting the surface or object with the products produced by the present processes. As used herein, "contacting" refers to placing a disinfecting composition comprising an effective concentration of peracid in contact with the surface or inanimate object suspected of contamination with a disease-causing entity for a period of time sufficient to clean and disinfect. Contacting includes spraying, treating, immersing, flushing, pouring on or in, mixing, combining, painting, coating, applying, affixing to and otherwise communicating a peracid solution or composition comprising an efficacious concentration of peracid, or a solution or composition that forms an efficacious concentration of peracid, with the surface or inanimate object suspected of being contaminated with a concentration of a microbial population.

The compositions comprising an efficacious concentration of peracid can also contain at least one additional antimicrobial agent, combinations of prion-degrading proteases, a virucide, a sporicide, or a biocide. Combinations of these agents with the peracid produced by the claimed processes can provide for increased and/or synergistic effects when used to clean and disinfect surfaces and/or objects contaminated (or suspected of being contaminated) with pathogenic microorganisms, viruses, fungi, and/or prions. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peracids formed by the present process can be used to reduce the concentration of microbial contaminants (e.g. a microbial population) when applied on and/or at a locus. As used herein, a "locus" of the invention comprises part or all of a target surface suitable for disinfecting or bleaching. Target surfaces include all surfaces that can potentially be contaminated with microorganisms, viruses, fungi, prions or combinations thereof. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment, (such as endoscopes) clothing worn in hospital/veterinary or other healthcare settings, including scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; and hatcheries for poultry or for shrimp. Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

Cephalosporin C Deacetylases

Cephalosporin C deacetylases (E.C. 3.1.1.41; systematic name cephalosporin C acetylydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven (CE-7; see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.)

The CE-7 family includes both CAHs and acetyl xylan esterases (AXEs; E.C. 3.1.1.72). CE-7 family members are quite unusual in that they typically exhibit ester hydrolysis activity for both acetylated xylooliogsaccharides and cephalosporin C, suggesting that the CE-7 family represents a single class of proteins with a multifunctional deacetylase activity against a range of small substrates (Vincent et al., *J. Mol. Biol.*, 330:593-606 (2003)). Vincent et al. describes the structural similarity among the members of this family and proposes a signature sequence motif characteristic of the CE-7 family.

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.*, 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.*, 54(3):406-412 (2000); Mitshushima et al., supra, Abbott, B. and Fukuda, D., *Appl. Microbiol.* 30(3):413-419 (1975); Vincent et al., supra, Takami at al., *NAR*, 28(21):4317-4331 (2000); Rey et al., *Genome Biol.*, 5(10): article 77 (2004); Degrassi et al., *Microbiology.*, 146:1585-1591 (2000); U.S. Pat. Nos. 6,645,233; 5,281,525; 5,338,676; and WO 99/03984. A non-comprehensive list of CE-7 family seven members having significant homology to SEQ ID NO: 2 are provided in Table 1.

TABLE 1

Example of CE-7 Enzymes Having Significant Homology to SEQ ID NO: 2.

| Source Organism (GenBank ® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| B. subtilis ATCC 31954 ™ | 1 | 2 | 100 | B. subtilis SHS 0133 Mitshushima et al., supra |

TABLE 1-continued

Example of CE-7 Enzymes Having Significant Homology to SEQ ID NO: 2.

| Source Organism (GenBank ® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| *B. subtilis* subsp. *subtilis* str. 168 (NP_388200) *B. subtilis* BE1010 | 5 | 6 | 98 | Kunst et al., supra. WO99/03984 Payne and Jackson, J. Bacteriol. 173: 2278-2282 (1991)) |
| *B. subtilis* ATCC 6633 (YP_077621.1) | 7 | 8 | 96 | U.S. Pat. No. 6,465,233 |
| *B. licheniformis* ATCC 14580 (YP_077621.1) | 9 | 10 | 77 | Rey et al., supra |
| *B. pumilis* (CAB76451.2) | 11 | 12 | 76 | Degrassi et al., supra |
| *Clostridium thermocellum* ATCC 27405 (ZP_00504991) | 13 | 14 | 57 | Copeland et al. US Dept. of Energy Joint Genome Institute (JGI-PGF) Direct Submission GenBank ® ZP_00504991 |
| *Thermotoga neapolitana* (AAB70869.1) | 15 | 16 | 42 | See GenBank ® AAB70869.1 |
| *Thermotoga maritima* MSB8 (NP_227893.1) | 17 | 18 | 42 | Nelson et al., Nature 399 (6734): 323-329 (1999) |
| *Thermoanaerobacterium* sp. (AAB68821.1) | 19 | 20 | 37 | Lorenz and Wiegel, supra |
| *Bacillus* sp. NRRL B-14911 (ZP_01168674) | 21 | 22 | 40 | Siefert et al. J. Craig Venter Institute. Direct Submission Under GenBank ® ZP_01168674 |
| *Bacillus halodurans* C-125 (NP_244192) | 23 | 24 | 36 | Takami et al., supra |
| *Bacillus clausii* KSM-K16 (YP_175265) | 25 | 26 | 33 | Kobayashi et al., Appl. Microbiol. Biotechnol. 43 (3), 473-481 (1995) |

Additional Substrates for Generating Peracids

Cephalosporin C deacetylases and acetylxylan esterases (E.C. 3.1.1.72) belong to the CE-7 family of carbohydrate esterases (Vincent et al., supra). CE-7 family carbohydrate esterases have been reported to hydrolyze acetyl group on acetylated polymeric xylan, acetylated xylose, acetylated glucose, and acetylated cellulose. As such, acetylated carbohydrates may be suitable substrates for generating percarboxylic acids using the present process (i.e., in the presence of a peroxygen source). Examples of acetylated carbohydrates include, but are not limited to acetylated glucose (such as glucose pentaacetate), acetylated mannose, acetylated xylose (such as xylose tetraacetate), and acetylated cellulose.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. Transcription, translation and the protein biosynthetic apparatus remain invariant relative to the cellular feedstock used to generate cellular biomass; functional genes will be expressed regardless. Examples of host strains include, but are not limited to bacterial, fungal or yeast species such as *Aspergillus, Trichoderma, Saccharomyces, Pichia, Phaffia, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In one embodiment, bacterial host strains include *Escherichia, Bacillus,* and *Pseudomonas*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived the preferred host cell.

Industrial Production

A variety of culture methodologies may be applied to produce the present perhydrolase catalysts. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process, the media is inoculated with the desired organism or organisms and growth or metabolic activity may occur without adding anything further to the system. Typically, however, a "batch" culture is batch with respect to the addition of carbon source and attempts are often made to control factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system except that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired products may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol (for example, when the host cell is a methylotrophic microorganism). Similarly, various species of *Candida* will metabolize alanine or oleic acid (Sulter et al., *Arch. Microbiol.*, 153:485-489 (1990)). Hence, it is contemplated that the source of carbon utilized in the present invention may encompass a wide variety of carbon-containing substrates and will only be limited by the choice of organism.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

General Methods

The following examples are provided to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliters, "mL" means milliliters, "L" means liters, "mM" means millimolar, "M" means molar, "mmol" means millimole(s), "ppm" means parts per million, "wt" means weight, "wt %" means weight percent, "g" means grams, "µg" means micrograms, "g" means gravity, "HPLC" means high performance liquid chromatography, "dd H$_2$O" means distilled and deionized water, "dcw" means dry cell weight, "ATCC" or "ATCC®" means the American Type Culture Collection (Manassas, Va.), "U" means units of perhydrolase activity, "rpm" means revolutions per minute, and "EDTA" means ethylenediaminetetraacetic acid.

EXAMPLE 1

Growth of *Bacillus subtilis* ATCC 31954™ and Preparation of Cell Extract

A culture of *Bacillus subtilis* (ATCC 31954™) was revived following suspension of the dried culture in 5 mL of nutrient broth (Difco; 0003-01-6) and incubation for 3 days at 30° C. Following the third day of incubation, an aliquot of the culture was streaked onto a trypticase soy agar culture plate (Becton, Dickinson, and Company; Franklin Lakes, N.J.) and incubated at 35° C. for 24 h. Several single colonies were scraped onto a 1 microliter inoculation loop (Becton Dickinson; catalog #220215) and transferred into 50 mL of *Lactobacillus* MRS broth (Hardy Diagnostics, Santa Maria, Calif.; catalog #C5931). The culture was then grown at 30° C. and a 200-rpm agitation rate for 12 h. After 12 h of growth, 2 mL of the culture was transferred into an unbaffled 500-mL shake flask containing 100 mL of MRS broth for growth at 30° C. and 200-rpm agitation for 12-14 h. The cells were subsequently harvested by centrifugation at 15,000×g for 25 min at 5° C. and the resulting cell paste stored at –80° C.

For cell extract preparation, 0.9 g of cell paste was suspended at 25 wt % (wet cell weight) in 0.05 M potassium phosphate buffer (pH 7.0) containing dithiothreitol (1 mM) and EDTA (1 mM). The cell suspension was passed twice through a French press having a working pressure of 16,000 psi. The crude extract was then centrifuged at 20,000×g to remove cellular debris, producing a clear cell extract that was assayed for total soluble protein (Bicinchoninic Acid Kit for Protein Determination, Sigma Aldrich, Sigma catalog #BCA1-KT), then frozen and stored at –80° C.

EXAMPLE 2

Determination of Perhydrolysis Activity of *Bacillus subtilis* ATCC 31954™ Semi-Purified Cell Extract A 1.0-mL aliquot of *Bacillus subtilis* (ATCC$^{31954}$™) cell extract (10 mg total protein/mL, prepared as described in Example 1) was diluted with an equal volume of 50 mM phosphate buffer (pH 7.0) and filtered through a 100,000 Molecular Weight Cutoff (MWCO) Centricon membrane unit (Millipore Corp, Bedford, Mass.). The resulting filtrate (semi-purified cell extract) contained 1.5 mg total protein/mL assayed for total soluble protein (Bicinchoninic Acid Kit for Protein Determination, Sigma catalog #BCA1-KT), and an assay of this filtrate indicated no measurable catalase activity.

A 1-mL reaction mixture containing triacetin (250 mM), hydrogen peroxide (2.5 M) and 0.100 mL of semi-purified cell extract (0.15 mg extract total protein) in 50 mM phosphate buffer (pH 6.5) was mixed at 25° C. A control reaction was run by substituting 50 mM phosphate buffer (pH 6.5) for semi-purified cell extract to determine the concentration of peracetic acid produced by chemical perhydrolysis of triacetin by hydrogen peroxide in the absence of added semi-purified cell extract.

Determination of the concentration of peracetic acid in the reaction mixture was performed according to the method described by Karst et al. Aliquots (0.250 mL) of the reaction mixture were removed at 10 min and 30 min and filtered using an Ultrafree® MC-filter unit (30,000 Normal Molecular Weight Limit (NMWL), Millipore cat #UFC3LKT 00) by centrifugation for 2 min at 12,000 rpm; removal of the protein component of the aliquot by filtration terminated the reaction. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC as described below. The peracetic acid concentrations produced in 10 min and 30 min is listed in Table 2.

HPLC Method:

Supelco Discovery C8 column (10-cm×4.0-mm, 5 µm) (cat. #569422-U) w/precolumn Supelco Supelguard Discovery C8 (Sigma-Aldrich; cat #59590-U); 10 microliter injection volume; gradient method with CH$_3$CN (Sigma-Aldrich; #270717) and deionized H$_2$O at 1.0 mL/min and ambient temperature:

| Time (min:sec) | (% CH₃CN) |
| --- | --- |
| 0:00 | 40 |
| 3:00 | 40 |
| 3:10 | 100 |
| 4:00 | 100 |
| 4:10 | 40 |
| 7:00 (stop) | 40 |

TABLE 2

Peracetic acid (PAA) produced by reaction of triacetin (250 mM) and hydrogen peroxide (2.5 M) at pH 6.5 in the presence or absence of *B. subtilis* (ATCC 31954 ™) semi-purified cell extract.

| *B. subtilis* (ATCC 31954 ™) semi-purified cell extract (mg total protein/mL) | peracetic acid (ppm) in 10 min | peracetic acid (ppm) in 30 min |
| --- | --- | --- |
| 0 | 641 | 1343 |
| 0.15 | 3492 | 3032 |

EXAMPLE 3

Perhydrolysis Activity of Semi-Purified Enzyme from *Bacillus subtilis* ATCC Cell Extract

*Bacillus subtilis* ATCC 31954™ growth and extract preparation was performed as described in Example 1, except that the crude extract was not centrifuged. The crude extract was fractionated with cold n-propanol (−20° C.). A flask containing the cell-free extract was stirred in an ice bath for 15 min, then the n-propanol (−20° C.) was added drop-wise (to prevent freezing of the extract) to a concentration of 40% (v/v). The resulting extract/propanol mixture was stirred in the ice bath for 30 min, then centrifuged at 12,000×g for 10 min at 5° C., and the supernatant returned to the flask and placed into the ice bath. Additional n-propanol (−20° C.) was slowly added to the supernatant with stirring to a concentration of 60% (v/v), and the resulting mixture stirred for 30 min in the ice bath and then centrifuged as before. The pellet from this second fraction was saved on ice and the supernatant returned to the flask and placed into the ice bath. Cold n-propanol was slowly added to the supernatant with stirring to a concentration of 80% (v/v), the mixture stirred for 30 min and centrifuged as before. The pellet from the 60-80% fraction was saved on ice. The pellets from the 40-60% (v/v) n-propanol fractions and the 60-80% (v/v) n-propanol fractions were dissolved in a minimum amount of 0.05 M phosphate buffer (pH 6.5) and the resulting solutions assayed for total soluble protein (Bicinchoninic Acid Kit for Protein Determination, catalog #BCA1-KT), then frozen and stored at −80° C.

A 1-mL reaction mixture containing triacetin (250 mM), hydrogen peroxide (1.0 M) and 0.10 mg/mL of total soluble protein from either the 40-60% (v/v) or 60-80% (v/v) n-propanol fractions of the cell extract (prepared as described above) in 50 mM phosphate buffer (pH 6.5) was mixed at 25° C. A control reaction was run by substituting 50 mM phosphate buffer (pH 6.5) for the n-propanol fractions of the cell extract containing semi-purified enzyme to determine the concentration of peracetic acid produced by chemical perhydrolysis of triacetin by hydrogen peroxide in the absence of added semi-purified enzyme. The reaction mixture was assayed for peracetic acid at 5 min and 30 min using the procedure described in Example 2, and the concentrations of peracetic acid produced by added enzyme are listed in Table 3.

TABLE 3

Peracetic acid (PAA) produced by reaction of triacetin (250 mM) and hydrogen peroxide (1.0 M) at pH 6.5 in the presence or absence of *B. subtilis* (ATCC 31954 ™) semi-purified cell extracts.

| n-propanol fraction of cell extract | total protein (mg/mL reaction) | peracetic acid (ppm) in 5 min | peracetic acid (ppm) in 30 min |
| --- | --- | --- | --- |
| no extract | 0 | 221 | 803 |
| 40-60% | 0.1 | 2829 | 4727 |
| 60-80% | 0.1 | 1832 | 3777 |

EXAMPLE 4

Identification of a Cephalosporin C Deacetylase Having Perhydrolysis Activity from *Bacillus subtilis* ATCC 31954™ Cell Extract A 0.1 mL sample (500 µg total protein) of the 40-60% n-propanol fraction described in Example 3 was mixed at room temperature with an equal volume of 2× non-denaturing (native) sample buffer (Invitrogen) and loaded into the preparative sample well of a 1.5 mm 8-16% Tris-Glycine polyacrylamide mini-gel (2D gels; Invitrogen). The native gel electrophoresis was operated at 125 V for 90 min using Tris-Glycine running buffer (Invitrogen). Following electrophoresis, the gel was prepared for an in situ esterase activity assay using the pH indicator, bromothymol blue.

The gel was washed for 10 min×2 with deionized water and slow mechanical mixing. The gel was then washed for 10 min using 10 mM phosphate buffer. Following the removal of the phosphate buffer, 50 mL of 10 mM phosphate buffer containing 665 µL of saturated bromothymol blue (in water) was incubated with the gel for 10 min followed by the addition of 1 mL of neat triacetin (Sigma Aldrich). Within 10 min of incubation one yellow band at 146 kD appeared on the gel indicating esterase activity.

The esterase-positive band was excised from the gel and transferred into a 50 mL polypropylene conical tube (Falcon). The yellow bromothymol blue stain was removed from the gel slice following 2-5 mL deionized water washes with gentle mixing. The gel slice was then treated for 30 min with 0.9 mL of 2× Novex Tris-Glycine SDS sample buffer plus 100 µL of 10× NuPAGE reducing agent (Invitrogen) with gentle mixing. Following the sample treatment, the gel slice and sample buffer were incubated at 85° C. for 5 min using a hot water bath. The gel slice was then removed from the incubation tube and carefully placed in the single preparative well of a 1.5 mm 8-16% Tris-Gly mini-gel. Care was taken to exclude air bubbles and to have direct contact with the stacking gel. The gel slice was then immobilized in place following the addition of 250-300 µL of a warm 0.5% agarose solution prepared in deionized water into the preparative well. The single molecular marker lane was loaded with 15 µL of See-Blue® Plus2 pre-stained MW marker (Invitrogen).

The electrophoresis of the gel slice was operated at 30 V for 30 min for electro-elution of the protein from the gel slice into the slab gel. The voltage was then ramped up from 30 V to 125 V over 10 min followed by 90 min operation at 125 V. Following electrophoresis, the resolved protein bands on the gel were blotted onto a PVDF membrane as described in the XCell II™ blotting manual (Invitrogen) and the blotting buffer was 10 mM CAPS, pH 11.0. The electro-blotting procedure was operated at 25 V for 2 hr at room temperature with ice water in the jacket of the transfer apparatus.

Following the transfer, the PVDF membrane was stained with ProBlot staining solution (Applied Biosystems, Foster City, Calif.) for 1 m followed by de-staining with methanol: water (50:50). Six protein bands were identified and each was N-terminal sequenced. Following a Blast search of the GenBank® amino acid sequence database, the only band having esterase-related sequence homology was identified as Band 1 and the 17 N-terminal amino acid calls had 100% amino acid identity to a *Bacillus subtilis* cephalosporin C deacetylase (GenBank® BAA01729; Mitsushima et al., supra; U.S. Pat. Nos. 5,528,152; and 5,338,676).

EXAMPLE 5

Cloning and Expression of Enzyme Having Perhydrolysis Activity from *Bacillus subtilis* ATCC 31954™

Genomic DNA was isolated from *Bacillus subtilis* ATCC 31954™ using the PureGene® DNA purification system (Gentra Systems, Minneapolis Minn.). The perhydrolase gene was amplified from the genomic DNA by PCR (0.5 min at 94 C, 0.5 min at 55 C, 1 min at 70, 30 cycles) using primers identified as SEQ ID NO: 3 (5'-ATGCAACTATTCGATCT-GCCGCTC-3') and SEQ ID NO: 4 (5'-TTATCAGCCTT-TAAGATGCTGCTTAA-3'). The resulting nucleic acid product (SEQ ID NO: 1) was subcloned into pTrcHis2-TOPO® (invitrogen, Carlsbad Calif.) to generate the plasmid identified as pSW186. The deduced amino acid sequence encoded by the expressed gene is provided as SEQ ID NO: 2.

The plasmid pSW186 was used to transform *E. coli* TOP10 (Invitrogen, Carlsbad Calif.), *E. coli* MG1655 (ATCC 47076™) and *E. coli* UM2 (*E. coli* Genetic Stock Center #7156, Yale University, New Haven Conn.) to generate the strains identified as TOP10/pSW186, MG1655/pSW186 and UM2/pSW186, respectively. TOP10/pSW186, MG1655/pSW186 and UM2/pSW186 were gown in LB media at 37° C. with shaking up to $OD_{600}$=0.4-0.5, at which time IPTG (isopropyl-β-D-thiogalactopyranoside) was added to a final concentration of 1 mM, and incubation continued for 2-3 hrs. Cells were harvested by centrifugation and SDS-PAGE was performed to confirm expression of the perhydrolase protein.

EXAMPLE 6

Evaluation of *Bacillus subtilis* ATCC 31954™ Perhydrolase Expressed in *E. coli* Transformants The three transformants described in Example 5 were grown in unbaffled shake flasks containing Miller's LB broth (50 mL; Mediatech, Inc, Herndon, Va.) with ampicillin (100 µg/mL) for 14-16 h at 35-37° C. with 200 rpm agitation. Following the overnight growth of the three transformants, each culture was sub-cultured by preparing a 1:100 dilution of each culture into fresh Miller's LB broth containing ampicillin (100 µg/mL). Following a 3 h growth at 35-37° C. with 200 rpm agitation, each culture was induced by the addition of IPTG to a final concentration of 1 mM. After an additional 3 hrs growth under the same conditions, the cell paste from each culture was harvested by centrifugation at 26,000×g for 20 min at 5° C. Cell extracts of each of the transformants were prepared according to the procedure described in Example 1, except that the extraction buffer used to prepare the 25 wt % wet cell suspension was composed of 0.05 M potassium phosphate (pH 7.0) and 1 mM dithiothreitol.

Separate 1-mL reactions containing triacetin (250 mM), hydrogen peroxide (1.0 M) and 50 µg of extract total protein from one of the three cell extracts (prepared as described above) in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. A second set of control reactions was run using 50 µg of extract total protein prepared from extracts of untransformed *E. coli* TOP10, *E. coli* MG1655 and *E. coil* UM2 to determine the background level of peracid produced by each strain in the absence of expressed perhydrolase. The concentration of peracetic acid in the reaction mixtures was determined according to the method of Karst et al., described in Example 2 (Table 4).

TABLE 4

Peracetic acid (PAA) produced by reaction of triacetin (250 mM) and hydrogen peroxide (1.0 M) at pH 6.5 in the presence of cell extracts of *E. coli* TOP10/pSW186, *E. coli* MG1655/pSW186 and *E. coli* UM2/pSW186.

| total protein extract source | total protein (µg/mL reaction) | peracetic acid (ppm) in 5 min | peracetic acid (ppm) in 30 min |
|---|---|---|---|
| no extract | 0 | 188 | 598 |
| TOP10 | 50 | 181 | 654 |
| TOP10/pSW186 | 50 | 2684 | 5363 |
| MG1655 | 50 | 173 | 638 |
| MG1655/pSW186 | 50 | 1354 | 4333 |
| UM2 | 50 | 175 | 655 |
| UM2/pSW186 | 50 | 3002 | 6529 |

EXAMPLE 7

Perhydrolytic Activity of *E. coli* TOP10/pSW186 Extract Expressing *Bacillus subtilis* ATCC 31954™ Perhydrolase Separate 1.0 mL triacetin perhydrolysis reactions were run as described in Example 6 using the *E. coli* TOP10/pSW186 transformant extract to provide one of the following total protein concentrations in the reaction: 196 µg/mL, 98 µg/mL, 49 µg/mL, 25 µg/mL, 12.5 µg/mL, 6.25 µg/mL, 3.0 µg/mL, or 1.5 µg/mL total protein concentration in each reaction (Table 5).

TABLE 5

Dependence of peracetic acid (PAA) concentration on total protein concentration derived from *E. coli* TOP10/pSW186 transformant extract in reactions containing triacetin (250 mM) and hydrogen peroxide (1.0 M) at pH 6.5.

| total protein extract source | total protein (µg/mL reaction) | peracetic acid (ppm) in 5 min | peracetic acid (ppm) in 30 min |
|---|---|---|---|
| no extract | 0 | 193 | 854 |
| TOP10 | 50 | 181 | 654 |
| TOP10/pSW186 | 1.5 | 580 | 1710 |
| TOP10/pSW186 | 3.0 | 824 | 2233 |
| TOP10/pSW186 | 6.3 | 1371 | 3029 |
| TOP10/pSW186 | 12.5 | 2052 | 4587 |
| TOP10/pSW186 | 25 | 2849 | 4957 |
| TOP10/pSW186 | 49 | 4294 | |
| TOP10/pSW186 | 98 | 4244 | |
| TOP10/pSW186 | 196 | 4294 | |

EXAMPLE 8

Perhydrolytic Activity of *E. coli* UM2/pSW186 Extract Expressing *Bacillus subtilis* ATCC 31954™ Perhydrolase An extract of *E. coli* UM2/pSW186 transformant (20 mg total protein/mL extract, prepared as described in Example 6) was employed in 1.0 mL perhydrolysis reactions (run as described in Example 6) containing triacetin (40 mM or 100 mM), hydrogen peroxide (40 mM or 100 mM) and extract total protein (0.1 mg/mL or 1.0 mg/mL) in phosphate buffer (Pi, 100 mM, 200 mM or 300 mM) at pH 6.5 or 7.5 at 25° C. each reaction (Table 6).

TABLE 6

Dependence of peracetic acid (PAA) concentration on triacetin and hydrogen peroxide concentrations using perhydrolase derived from *E. coli* UM2/pSW186 transformant extract at pH 6.5 or 7.5.

| total protein (mg/mL) | $H_2O_2$ (mM) | triacetin (mM) | Pi (mM) | pH | PAA (ppm) in 5 min | PAA (ppm) in 30 min |
|---|---|---|---|---|---|---|
| 0 | 40 | 40 | 100 | 6.5 | 0 | 0 |
| 0 | 40 | 100 | 100 | 6.5 | 0 | 0 |
| 0.1 | 40 | 40 | 100 | 6.5 | 49 | 0 |
| 1 | 40 | 40 | 100 | 6.5 | 239 | 160 |
| 1 | 40 | 100 | 100 | 6.5 | 439 | 560 |
| 0 | 40 | 100 | 200 | 6.5 | 0 | 0 |
| 0 | 100 | 100 | 200 | 6.5 | 1 | 30 |
| 0 | 100 | 100 | 200 | 7.5 | 14 | 1 |
| 0 | 100 | 100 | 300 | 7.5 | 5 | 4 |
| 1 | 100 | 40 | 200 | 6.5 | 75 | 9 |
| 1 | 100 | 100 | 200 | 6.5 | 1150 | 925 |
| 1 | 40 | 100 | 200 | 7.5 | 290 | 80 |
| 1 | 100 | 100 | 300 | 7.5 | 332 | 58 |

EXAMPLE 9

Cloning and Expression of Perhydrolase from *Bacillus subtilis* BE1010

Genomic DNA was isolated from *Bacillus subtilis* BE1010 (Payne and Jackson, *J. Bacterial.* 173:2278-2282 (1991)) using the PureGene DNA purification system (Gentra Systems, Minneapolis Minn.). The coding region of the perhydrolase gene (SEQ ID NO: 5 encoding SEQ ID NO: 6) was amplified from the genomic DNA by PCR (0.5 min at 94° C., 0.5 min at 55 C, 1 min at 70, 30 cycles) using primers identified as SEQ ID NO: 1 and SEQ ID NO: 2. The resulting nucleic acid product was subcloned into pTrcHis2-TOPO (Invitrogen, Carlsbad Calif.) to generate the plasmid identified as pSW187. Plasmid pSW187 The plasmid pSW187 was used to transform *E. coli* TOP10 (Invitrogen, Carlsbad Calif.), *E. coli* MG1655 (ATCC 47076) and *E. coli* UM2 (*E. coli* Genetic Stock Center #7156, Yale University, New Haven Conn.) to generate the strains identified as TOP10/pSW187, MG1655/pSW187 and UM2/pSW187, respectively. TOP10/pSW187, MG1655/pSW187 and UM2/pSW187 were gown in LB media at 37° C. with shaking up to $OD_{600}$=0.4-0.5, at which time IPTG was added to a final concentration of 1 mM, and incubation continued for 2-3 hrs. Cells were harvested by centrifugation and SDS-PAGE was performed to confirm expression of the perhydrolase protein.

EXAMPLE 10

Evaluation of Perhydrolase Expressed in *E. coli* Transformants Derived from *Bacillus subtilis* BE1010

The *E. coil* TOP10/pSW187, *E. coli* MG1655/pSW187 and *E. coli* UM2/pSW187 transformants described in Example 9 were grown in unbaffled shake flasks containing Miller's LB broth (50 mL; Mediatech, Inc, Hemdon, Va.) with ampicillin (100 µg/mL) for 14-16 h at 35-37° C. with 200 rpm agitation. Following the overnight growth of the three transformants, each culture was sub-cultured by preparing a 1:100 dilution of each culture into fresh Miller's LB broth containing ampicillin (100 µg/mL). Following a 3 hour growth at 35-37° C. with 200 rpm agitation, each culture was induced by the addition of IPTG to a final concentration of 1 mM. After an additional 3 hours growth under the same conditions, the cell paste from each culture was harvested by centrifugation at 26,000×g for 20 min at 5° C. For cell extract preparation, the procedure described in Example 1 was repeated except that the extraction buffer used to prepare the 25 wt % wet cell suspension was composed of 0.05 M potassium phosphate (pH 7.0) and 1 mM dithiothreitol.

Separate 1.0 mL reactions containing triacetin (250 mM), hydrogen peroxide (1.0 M) and 50 µg of extract total protein in 50 mM phosphate buffer (pH 6.5) were run at 25° C. with each transformant extract. A control reaction was run substituting 50 mM phosphate buffer (pH 6.5) for the extract total protein solution to determine the concentration of peracetic acid produced by chemical perhydrolysis of triacetin with hydrogen peroxide. A second set of control reactions was run using 50 µg of extract total protein prepared from extracts of untransformed *E. coli* TOP10, *E. coli* MG1655 and *E. coli* UM2 to determine the background level of peracid produced by each strain in the absence of expressed perhydrolase. The concentration of peracetic acid in the reaction mixtures (Table 7) was determined according to the method of Karst et al. as described in Example 2.

TABLE 7

Peracetic acid (PAA) produced by reaction of triacetin (250 mM) and hydrogen peroxide (1.0 M) at pH 6.5 in the presence of cell extracts of *E. coli* TOP10/pSW187, *E. coli* MG1655/pSW187 and *E. coli* UM2/pSW187.

| total protein extract source | total protein (µg/mL reaction) | peracetic acid (ppm) in 5 min | peracetic acid (ppm) in 30 min |
|---|---|---|---|
| no extract | 0 | 159 | 626 |
| TOP10 | 50 | 181 | 654 |
| TOP10/pSW187 | 50 | 3192 | 6663 |
| MG1655 | 50 | 173 | 638 |
| MG1655/pSW187 | 50 | 3472 | 7349 |
| UM2 | 50 | 175 | 655 |
| UM2/pSW187 | 50 | 3741 | 7626 |

What is claimed is:

1. A process for producing a peroxycarboxylic acid from a carboxylic acid ester comprising
a) providing a set of reaction components, said components comprising:
1) a carboxylic acid ester selected from the group consisting of:
i) esters having the structure

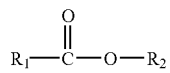

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2-O)_nH$ or $(CH_2CH(CH_3)-O)_nH$ and n=1 to 10; and
ii) glycerides having the structure

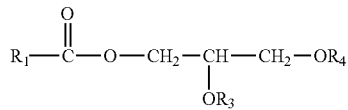

wherein $R_1$=C1 to C7 straight chain or branched chain alkyl optionally substituted with an hydroxyl or a C1 to C4 alkoxy group and $R_3$ and $R_4$ are individually H or $R_1C(O)$;
2) a source of peroxygen; and
3) an enzyme catalyst having perhydrolase activity, wherein said enzyme catalyst comprises a member selected from the group consisting of:
an enzyme having at least 95% amino acid identity to the polypeptide of SEQ ID NO: 6; and
(ii) a polypeptide encoded by a nucleic acid sequence that hybridizes to the polynucleotide of SEQ ID NO: 5 under the following conditions: 0.1×SSC, 0.1% SDS at 65° C. and washed with 2×SSC, 0.1% SDS at 65° C., followed by a second wash with 0.1×SSC, 0.1% SDS at 65° C.; and
b) combining said reaction components under suitable aqueous reaction conditions, wherein said conditions comprise a pH range of about 2 to about 9, whereby a peroxycarboxylic acid is produced.

2. The process of claim 1 wherein the peroxycarboxylic acid is produced at a concentration of at least 20 ppm of the product mixture within about 5 minutes to about 2 hours of combining the reaction components.

3. The process of claim 1 wherein the pH range is about 3 to about 7.

4. The process of claim 3 wherein the pH range is about 4 to about 6.5.

5. The process of claim 1 wherein the ester is selected from the group consisting of methyl lactate, ethyl lactate, methyl glycolate, ethyl glycolate, methyl methoxyactetate, ethyl methoxyacetate, methyl 3-hydroxybutyrate, ethyl 3-hydroxybutyrate, and mixtures thereof.

6. The process of claim 1 wherein the glyceride substrate is selected from the group consisting of monoacetin, diacetin, triacetin, monopropionin, dipropionin, tripropionin, monobutyrin, dibutyrin, tributyrin, and mixtures thereof.

7. The process of claim 1 wherein the peroxycarboxylic acid produced is selected from the group consisting of peracetic acid, perpropionic acid, perbutyric acid, perlactic acid, perglycolic acid, permethoxyacetic acid, per-β-hydroxybutyric acid, and mixtures thereof.

8. The process of claim 7 wherein the peroxycarboxylic acid produced is peracetic acid.

9. A process to reduce a concentration of a microbial population on a hard surface or inanimate object using an enzymatically produced peroxycarboxylic acid composition, said process comprising:
a) providing a set of reaction components, said components comprising:
1) a substrate selected from the group consisting of:
i) esters having the structure

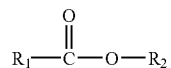

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2-O)_nH$ or $(CH_2CH(CH_3)-O)_nH$ and n=1 to 10; and ii) glycerides having the structure

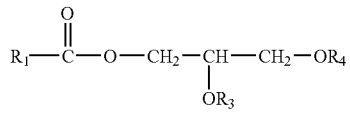

wherein $R_1$=C1 to C7 straight chain or branched chain alkyl optionally substituted with an hydroxyl or a C1 to C4 alkoxy group and $R_3$ and $R_4$ are individually H or $R_1C(O)$;
2) a source of peroxygen; and
3) an enzyme catalyst having perhydrolase activity, wherein said enzyme catalyst comprises a member selected from the group consisting of:
 (i) an enzyme having at least 95% amino acid identity to the polypeptide of SEQ ID NO: 6;
 (ii) a polypeptide encoded by a nucleic acid sequence that hybridizes to the polynucleotide of SEQ ID NO: 5 under the following conditions: 0.1×SSC, 0.1% SDS at 65° C. and washed with 2×SSC, 0.1% SDS at 65° C., followed by a second wash with 0.1×SSC, 0.1% SDS at 65° C.; and
 (iii) at least one of *Bacillus subtilis* BE1010 cell, permeabilized *Bacillus subtilis* BE1010 cell, cell component of a *Bacillus subtilis* BE1010 cell extract, partially purified enzyme perhydrolase from *Bacillus subtilis* BE1010, or purified enzyme from *Bacillus subtilis* BE1010;
b) combining said reaction components under suitable aqueous reaction conditions, wherein said conditions comprise a pH range of about 2 to about 9, whereby a peroxycarboxylic acid product is formed;
c) optionally diluting the peroxycarboxylic acid product; and
d) contacting a hard surface or inanimate object having a concentration of microbial contaminants with the peroxycarboxylic acid produced in step b) or step c) whereby the concentration of microbial contaminants is reduced at least 3-log.

10. The process of claim 9 wherein the peroxycarboxylic acid product formed in step b) comprises a peroxycarboxylic acid concentration of at least 20 ppm of the product mixture within about 5 minutes to about 2 hours of combining the reaction component.

11. The process of claim 9 wherein the hard surface or inanimate object is contacted with the peroxycarboxylic acid produced in step b) or step c) within about 5 minutes to about 168 hours of combining said reaction components.

12. The process of claim 9 wherein the hard surface or the inanimate object is contacted with the peroxycarboxylic acid produced in step b) or step c) within about 5 minutes to about 48 hours of combining said reaction components.

13. The process of claim 9 wherein the hard surface or the inanimate object is contacted with the peroxycarboxylic acid produced in step b) or step c) within about 5 minutes to about 2 hours of combining said reaction components.

14. The process according to any one of claims 9 to 13 wherein the concentration of microbial contaminants is reduced at least 5-log.

15. The process of claim 9 wherein the pH range is about 3 to about 8.

16. The process of claim 15 wherein the pH range is about 4 to about 6.5.

17. The process of claim 9 wherein the ester substrate is selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, and mixtures thereof.

18. The process of claim 17 wherein the ester substrate is selected from the group consisting of ethyl lactate, ethyl acetate, and mixtures thereof.

19. The process of claim 9 wherein the glyceride substrate is selected from the group consisting of monoacetin, diacetin, triacetin, monopropionin, dipropionin, tripropionin, monobutyrin, dibutyrin, tributyrin, and mixtures thereof.

20. The process of claims 1 or 9 wherein the peroxycarboxylic acid is produced at a concentration of at least about 200 ppm of the product mixture within about 5 minutes.

21. The process of claim 20 wherein the peroxycarboxylic acid is produced at a concentration of at least about 1000 ppm of the product mixture within about 5 minutes.

22. The process of claim 21 wherein the peroxycarboxylic acid is produced at a concentration of at least about 2000 ppm of the product mixture within about 5 minutes.

23. The process of claim 9 wherein the peroxycarboxylic acid produced is selected from the group consisting of peracetic acid, perpropionic acid, perbutyric acid, perlactic acid, perglycolic acid, permethoxyacetic acid, per-β-hydroxybutyric acid, and mixtures thereof.

24. The process of claim 23 wherein the peroxycarboxylic acid produced is peracetic acid.

25. The process of claim 1 or 9 wherein the enzyme catalyst having perhydrolase activity is an enzyme having the amino acid sequence set forth in SEQ ID NO:6.

* * * * *